United States Patent [19]
Pratt et al.

[11] Patent Number: 5,607,436
[45] Date of Patent: Mar. 4, 1997

[54] APPARATUS FOR APPLYING SURGICAL CLIPS

[75] Inventors: James R. Pratt, Wolcott; Gary S. Kappel, Stamford; Douglas J. Cuny, Bethel; H. Jonathan Tovey, Milford; Paul J. Phillips, Middlebury; Mark S. Peyser, Monroe; Ernie Aranyi, Easton, all of Conn.

[73] Assignee: United States Surgical Corporation, Norwalk, Conn.

[21] Appl. No.: 134,347

[22] Filed: Oct. 8, 1993

[51] Int. Cl.$^6$ .................................................. A61B 17/00
[52] U.S. Cl. ........................... 606/143; 606/139; 227/901
[58] Field of Search ..................................... 606/139, 142, 606/143, 205–208; 227/901, 19, 175–182

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 3,955,581 | 5/1976 | Spasiano et al. . |
| 4,027,510 | 6/1977 | Hiltebrandt . |
| 4,152,920 | 5/1979 | Green . |
| 4,166,466 | 9/1979 | Jarvik . |
| 4,185,762 | 1/1980 | Froehlich . |
| 4,188,953 | 2/1980 | Klieman et al. . |
| 4,196,836 | 4/1980 | Becht . |
| 4,226,242 | 10/1980 | Jarvik . |
| 4,228,895 | 10/1980 | Larkin . |
| 4,242,902 | 1/1981 | Green . |
| 4,246,903 | 1/1981 | Larkin . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,394,864 | 7/1983 | Sandhaus . |
| 4,412,539 | 11/1983 | Jarvik . |
| 4,425,915 | 1/1984 | Ivanov . |
| 4,430,997 | 2/1984 | DiGiovanni et al. . |
| 4,450,839 | 5/1984 | Transue . |
| 4,452,357 | 6/1984 | Klieman et al. . |
| 4,452,376 | 6/1984 | Klieman et al. . |

(List continued on next page.)

FOREIGN PATENT DOCUMENTS

| | | |
|---|---|---|
| 0068046 | 1/1983 | European Pat. Off. . |
| 0406724 | 1/1991 | European Pat. Off. . |
| 0409569 | 1/1991 | European Pat. Off. . |
| 500353A1 | 8/1992 | European Pat. Off. ............... 606/143 |
| 2546696 | 4/1976 | Germany . |
| 8202825 | 9/1982 | WIPO . |
| 8910094 | 11/1989 | WIPO . |

OTHER PUBLICATIONS

Information Booklet for "Auto Suture® Premium Surgiclip™ Titanium Disposable Automatic Clip Appliers", ©1988, 1989.
"Ligaclip for Security in Ligation", Ethicon, 1982.
"Deep Surgery Advantage Dramatic New Access Plus Automatic-Feed in Vessel Ligation", Weck, Surgery, Gynecology & Obstetrics, Sep. 1986.
"New Surgical Procedures for Indirect Hernias", Innovative Surgical Devices, Inc., 1989.

Primary Examiner—Jeffrey A. Schmidt

[57] ABSTRACT

An apparatus is provided for applying surgical clips which includes provisions for applying a partially closed clip to ducts or shunts during a surgical procedure such as cholecystectomy procedures. The apparatus includes means for effecting a partial closing stroke of the handle mechanism to correspond to a partial closure of the jaw members, and permits a partial opening stroke to release the partially closed clip in the jaw mechanism. Other features of the invention include means for preventing over advancement of a clip to the jaw mechanism, means for cradling the clip as it is advanced from the clip supply to the jaw mechanism, means for preventing splaying of the jaws in the event of a clip-over-clip application, and a novel rotation collar. The instrument of the present invention provides the surgeon with visual, audible, and tactile indication of the positioning of the jaw members to effect the application of a partially closed clip.

74 Claims, 21 Drawing Sheets

U.S. PATENT DOCUMENTS

| | | |
|---|---|---|
| 4,471,780 | 9/1984 | Menges et al. . |
| 4,480,641 | 11/1984 | Failla et al. . |
| 4,492,232 | 1/1985 | Green . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,556,058 | 12/1985 | Green . |
| 4,557,263 | 12/1985 | Green . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,646,740 | 3/1987 | Peters et al. . |
| 4,662,373 | 5/1987 | Montgomery et al. . |
| 4,674,504 | 6/1987 | Klieman et al. . |
| 4,712,549 | 12/1987 | Peters et al. . |
| 4,850,355 | 7/1989 | Brooks et al. . |
| 4,944,443 | 7/1990 | Oddsen et al. . |
| 4,967,949 | 11/1990 | Sandhaus . |
| 5,030,226 | 7/1991 | Green et al. . |
| 5,047,038 | 9/1991 | Peters et al. . |
| 5,049,152 | 9/1991 | Simon et al. . |
| 5,067,958 | 11/1991 | Sandhaus . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,163,945 | 11/1992 | Ortiz et al. . |
| 5,171,247 | 12/1992 | Hughett et al. . |
| 5,171,249 | 12/1992 | Stefanchik et al. . |
| 5,176,702 | 1/1993 | Bales et al. ............... 606/208 |
| 5,192,288 | 3/1993 | Thompson et al. . |
| 5,199,566 | 4/1993 | Ortiz et al. . |
| 5,207,691 | 5/1993 | Nardella . |
| 5,246,156 | 9/1993 | Rothfuss et al. . |
| 5,246,450 | 9/1993 | Thornton et al. . |
| 5,258,007 | 11/1993 | Spetzler et al. ............ 606/208 |
| 5,282,807 | 2/1994 | Knoepfler . |
| 5,282,808 | 2/1994 | Kovac et al. . |
| 5,290,299 | 3/1994 | Fain et al. . |
| 5,306,280 | 4/1994 | Bregen et al. . |
| 5,333,772 | 8/1994 | Rothfuss et al. . |

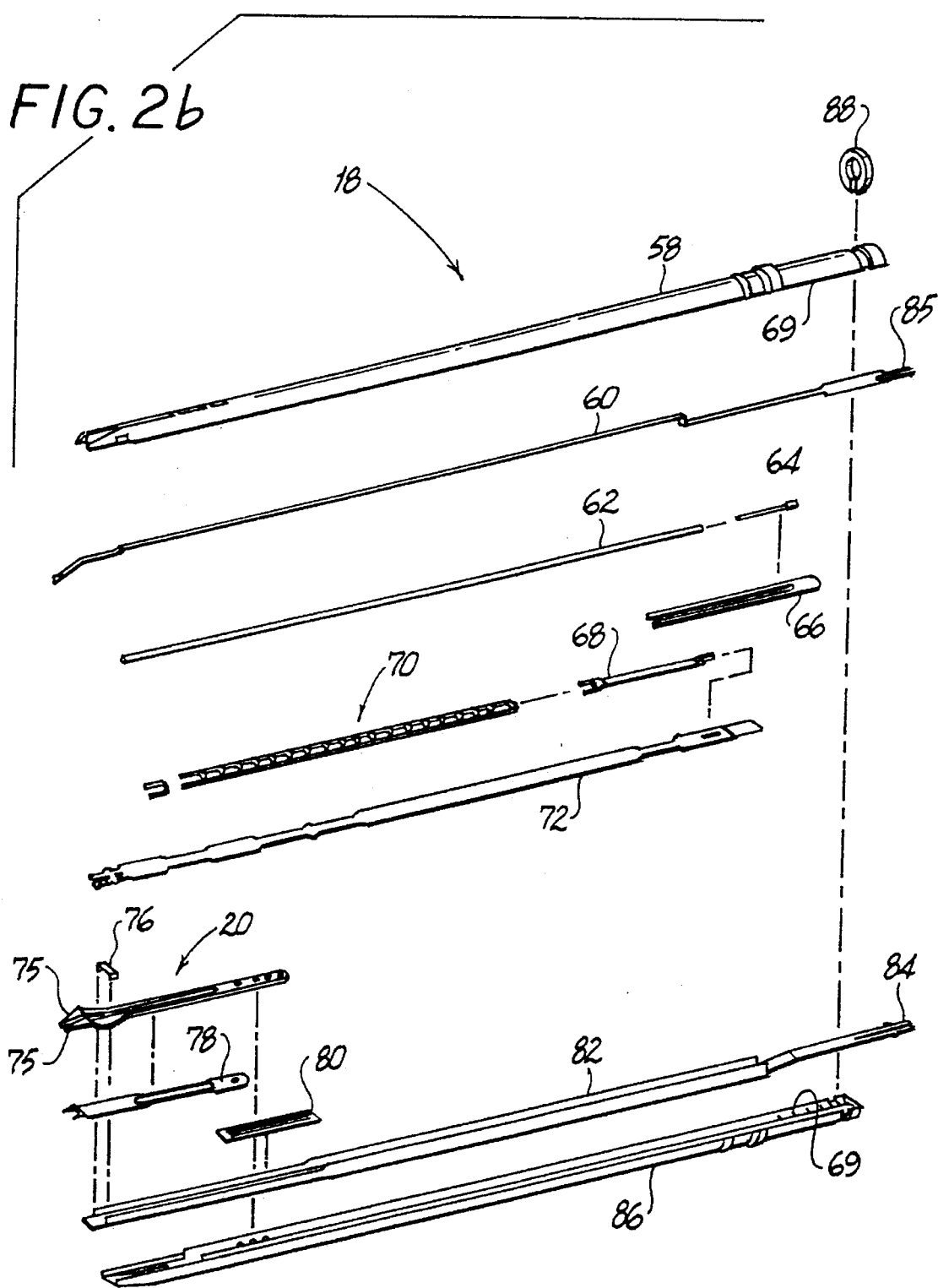

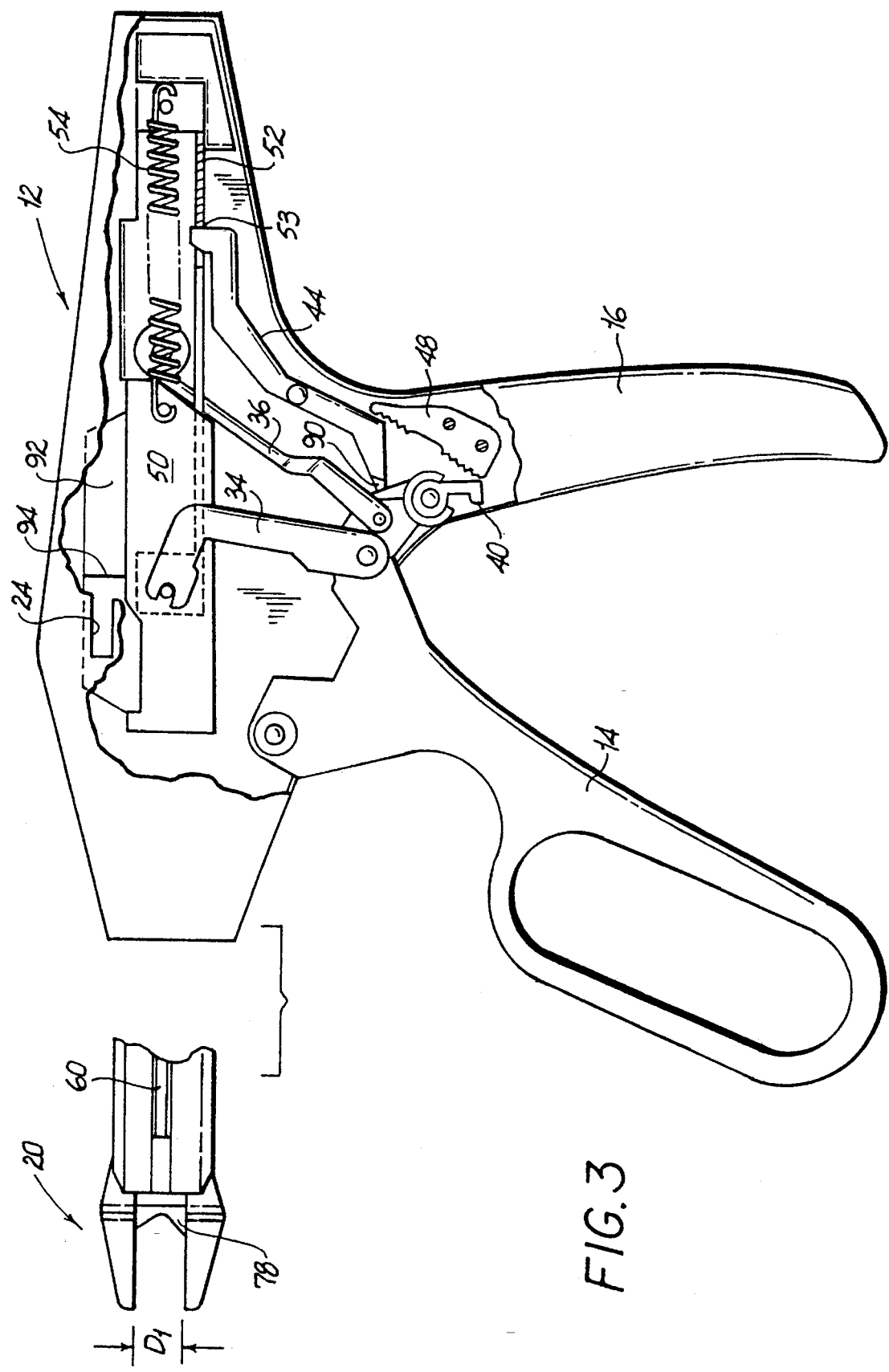

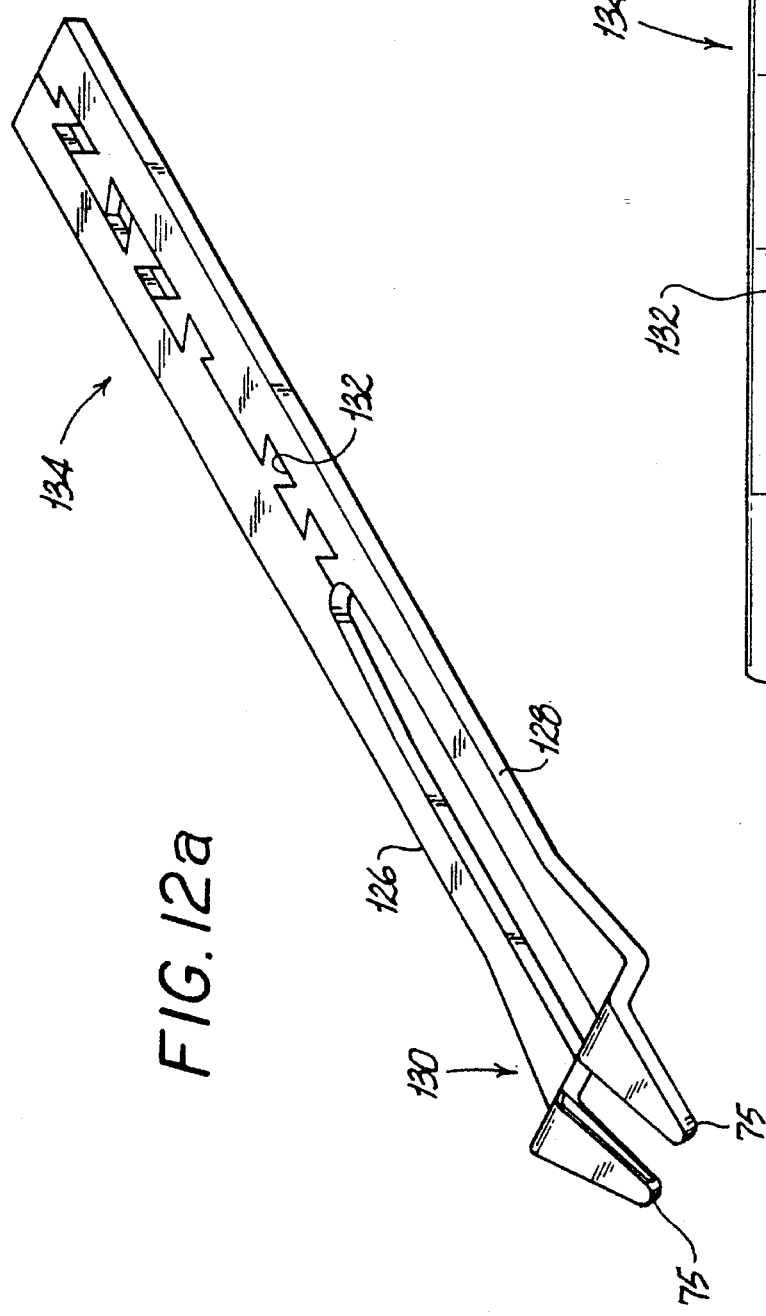
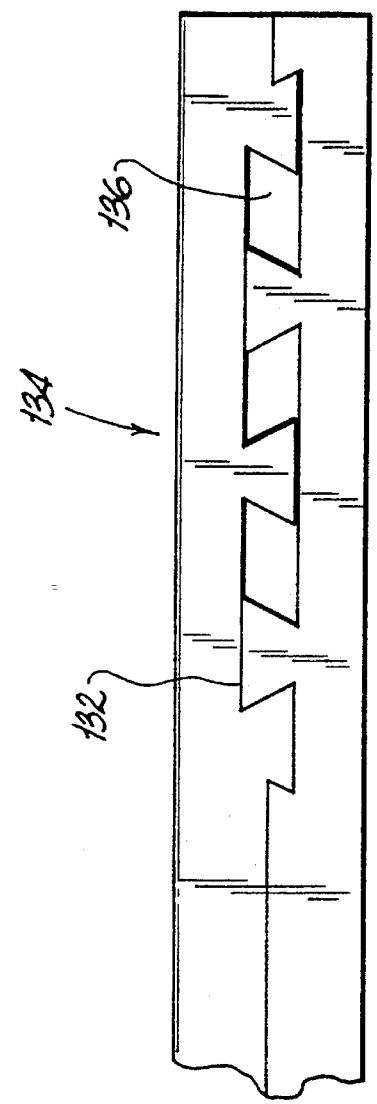
FIG. 12a
FIG. 12b

APPARATUS FOR APPLYING SURGICAL CLIPS

BACKGROUND OF THE INVENTION

1. Field of the Invention

This invention relates to an apparatus for applying surgical clips to body tissue during laparoscopic or endoscopic procedures, and more particularly, to a surgical clip applier adapted to apply fully crimped clips as well as a partially formed clip during surgical procedures.

2. Description of Related Art

In laparoscopic and endoscopic surgical procedures, a small incision is made in the patient's body to provide access for a robe or cannula device. Once extended into the patient's body, the cannula provides an access port which allows insertion of various surgical instruments through the cannula for acting on organs, blood vessels, ducts, or body tissue far removed from the incision. Often during these procedures, it is necessary to apply hemostatic clips to blood vessels or various ducts to prevent the flow of body fluids therethrough during the procedure. Many limes, the surgical procedure may necessitate the temporary implantation of shunts or tubes into ducts or vessels. Such procedures, such as gall bladder surgery, often require the placement of a shunt into the ducts during excision of the organ. To secure the shunt, a clip must be applied which is partially closed so as to avoid occluding the shunt. While instruments for performing surgical clip application are known in the art, none provide indication of the successful application of a partially crimped clip, such as is necessary to secure the shunt. Fully crimping a clip over a shunt will obviously occlude the shunt and defeat its purpose.

One clip applier known well in the art is described in U.S. Pat. No. 5,084,057, the disclosure of which is incorporated herein by reference. This instrument includes a mechanism for sequentially advancing a plurality of surgical clips towards a pair of distal jaw members. Through actuation of handle structure, the jaw members are closed to advantageously crimp the clip. The instrument does not provide an indication of the spacing between the jaws during the closing of the jaw members, other than through visual examination of the jaw members through an endoscope. Thus, when attempting to detachably secure a shunt to tissue, e.g., for cholangiography, it can be difficult to ascertain whether the jaw members have closed to an appropriate gap for securing the shunt.

Furthermore, many instruments now incorporate ratchet mechanisms to prevent inadvertent opening of the handles and jaws until the clip is fully crimped, requiring a full closing stroke. Thus, the instruments are not designed to deliver a partially crimped clip.

It has been common for clip appliers to rely on friction to capture a clip between the jaw members following advancement of the clip from the clip supply. Accordingly, the jaw members are constructed so as to have a gap between the crimping surface of each jaw member which is slightly less than the distance between the legs of a clip, so that the clip is slightly pinched between the jaws to hold the clip therein.

Another method of maintaining the clip within the jaws is to machine the crimping surfaces of the jaw members to have a clip accepting slot. However, this increases cost and requires precision during the machining process to provide the proper dimensions for end use. The jaw members are typically a costly item since they are machined from a single piece to form the crimping surfaces.

In view of this, it has been known to fabricate the jaw members separately, and then to assemble the jaw mechanism in the clip applying instrument. However, in instruments such as those disclosed in U.S. Pat. Nos. 5,047,038; 4,246,903 and 4,228,895, the jaws are hinged at a pivot point and do not provide reliable securements and accurate camming.

Should the jaw members be improperly gapped or aligned, the clip tends to fall out of the jaws, and potentially, into the patient's body. In addition, the clip advancement mechanism may not properly orient the clip if the jaws are not properly spaced. While some instruments may provide some clip alignment feature or clip stop mechanism, these are typically internal mechanisms which operate in conjunction with the clip supply, not the jaw mechanisms, such as disclosed in U.S. Pat. Nos. 5,192,288 and 4,616,650. Finally, should the clip become dislodged, or slightly deviate off-line, there is no provision in the prior art for holding or guiding the clip into the jaws. While some instruments may provide tabs to align the clip at the clip supply, such as disclosed in U.S. Pat. No. 4,492,262, there is no provision to support the clip outside the instrument at the jaws.

It is also common, due to the restricted space at the surgical site in which the clip appliers are used, that at times a clip may be applied which is interfered with by a clip that has previously been applied, leading to a splaying of the jaws beyond the original gap between the jaw members. Depending on the strength of the jaw members, this may lead to an improper feeding of a subsequent clip to the jaws, resulting in potential instrument malfunction.

It has been long known to provide instruments having a means for rotating the instrument with respect to its longitudinal orientation, typically through the provision of a rotation collar positioned at the juncture between the handle and elongated body portions of the instrument. Despite the multitude of prior art rotatable surgical instruments, a need exists to optimize the rotation collar to provide for more facile rotation capabilities.

Those skilled in the surgical arts have recognized the need for a clip applicator which may be used in endoscopic or laparoscopic procedures such as gall bladder operations which is configured to partially close and release a clip to secure shunts during the procedure. In addition, a need exists for a clip applier which accurately advances and holds a clip in the jaw mechanism and which prevents splaying of the jaws in the event of a clip over clip application. An instrument is also needed which provides a visual indication of the position of the jaw mechanism, and may also provide an audible and tactile indication. An instrument is also needed which prevents feeding of a clip in the event the jaws are not fully opened, as well as an instrument which provides for facile rotation of the instrument's body portion.

SUMMARY OF THE INVENTION

A novel clip applier of the present invention obviates the disadvantages encountered in the prior art and provides a cost-effective instrument which ensures accurate and efficient application of clips during a surgical procedure. The clip applier of the present invention provides an instrument which allows the surgeon to apply partially closed clips during a gall bladder operation to permit securement of shunts in organs without occluding the shunt, and provides visual, audible and/or tactile indication of when the jaws are in a predetermined position to permit the surgeon to release pressure on the handles to release the partially closed clip.

The instrument of the present invention substantially reduces the possibility of clips inadvertently falling out of the jaws, and prevents splaying of the jaws beyond the initial clip-receiving gap between the crimping surfaces in the event a clip is applied over a previously applied clip. The instrument also prevents a clip from being fed to the jaws in the event the jaws are not fully opened, and includes a clip holding feature associated with the clip advancing mechanism to hold a clip to ensure correct positioning between the jaw members. The instrument also permits facile rotation of body portion with respect to its longitudinal orientation through the provision of a novel rotation collar.

In accordance with the present invention, an apparatus is disclosed for applying surgical clips to vessels and ducts in a patient which comprises a handle portion, a body portion which extends distally from the handle portion, a clip supply for storing a plurality of surgical clips in a position for sequential advancement towards a distal end of the body portion, a jaw mechanism disposed at the distal end of the body portion which is movable between an open position for receiving a clip and a closed position for forming a clip in response to movement of the handle potion, means for advancing a clip from the clip supply to the jaw mechanism and means which will affect a partial closure of a clip positioned in the jaw mechanism. The closing mechanism provides a means for affecting a closing stroke of the jaw mechanism from the open position to the closed position and includes means for permitting at least a partial opening stroke of the jaw mechanism after at least a partial closing stroke is completed. The instrument provides the surgeon with a means for crimping a clip partially and then opening the jaws a sufficient distance to release the partially closed clip. The closing mechanism of the instrument requires a full closing stroke of the handle mechanism prior to feeding a subsequent clip to the jaw mechanism. The present invention provides the surgeon with an apparatus which will allow him to apply surgical clips to ducts within the body and further provides a means for the temporary implantation of shunts or robes in ducts by allowing partial closure of a clip without fully forming the clip to prevent occlusion of the duct or implanted shunt.

The instrument provides a tactile indication of the position of the jaw mechanism so that the surgeon knows when the jaw mechanism has closed a sufficient distance to place the jaws in a predetermined zone or position in which the clip is partially closed for application to the duct or shunt at the surgical site. The instrument may further provide audible indication of the position of the jaws in the predetermined zone, and further may include visual indication means which will give the surgeon a visual indication of when the jaws are in the predetermined zone. The instrument allows the surgeon to partially open the handle mechanism to release pressure on the partially closed clip to allow the clip to be removed or released from the jaw mechanism. Upon release of the partially closed clip, the surgeon continues the closing stroke to reset the instrument to place it in a position for a subsequent use.

The tactile and audible indicators essentially comprise a ratchet mechanism positioned within the handle portion of the clip applying instrument of the present invention. The ratchet mechanism includes a rack member positioned within the handle portion and a pawl member which is preferably positioned on the pivoting handle of the handle portion. The pawl member engages the rack member upon commencement of the closing stroke of the handle portion. Once the pawl member engages the rack, the movable handle is permitted to move in a closing direction towards the stationary hand grip, but is prevented from moving in an opening stroke away from the stationary hand grip. When the movable handle has travelled a sufficient distance, and the jaw mechanism has closed a corresponding sufficient distance so that a clip positioned between the jaw members is partially closed, the pawl member is released from the rack member, which allows the surgeon to effect a partial opening stroke of the movable handle, which provides a corresponding partial opening stroke of the jaw mechanism, and the partially closed clip is released from the jaw mechanism. The partial opening stroke of the handle portion will terminate when the pawl member re-engages the rack member and in order to reuse the instrument, the surgeon must complete the closing stroke of the movable handle of the handle portion.

The rack and pawl assembly provides an audible indication of when the jaw members are in the proper zone to effect release of the partially closed clip. As the pawl travels over the rack, an audible clicking sound may be heard as the pawl passes over the teeth of the rack member. When the jaw members are in the proper position, i.e., the jaws are partially closed to partially close a clip position therebetween, the pawl member leaves the teeth of the rack member so that the clicking sound has ceased. Upon this audible indication, the surgeon will know that a partial opening stroke may be affected to release the clip positioned between the jaws. The pawl will then re-engage the rack member to terminate the opening stroke, and the surgeon knows that he must complete the closing stroke to reload the instrument. The pawl and rack mechanism also provides the surgeon with a tactile indication by allowing him to "feel" the instrument when it is in the predetermined zone for partial closure of a clip. As the surgeon moves the movable handle towards the stationary hand grip and the pawl passes over the teeth of the rack, the surgeon can feel the clicking of the pawl over the teeth of the rack. When the pawl leaves the rack, and the surgeon no longer feels the pawl passing over the teeth of the rack, he will know that the jaws are in the predetermined zone for partially closing a clip, and can release the force on the movable handle to effect a partial opening stroke of the movable handle and allow the partially closed clip to be released from the jaw mechanism.

The ratchet mechanism disclosed in the handle portion preferably comprises a rack member having a plurality of teeth over a first distance and a plurality of teeth over a second distance which is separated by a space having no teeth. When the pawl member travels to the space having no teeth, the surgeon will know that the jaw mechanism is positioned within the predetermined zone for releasing the partially closed clip. Alternatively, the rack member may comprise a pair of rack members positioned in a series relationship which is separated by a distance. As the pawl member travels the distance between the two rack members, the surgeon will know that the jaw members are in the predetermined zone to release the partially closed clip. As a further alternative embodiment, the rack member may include teeth over a distance corresponding to a partial closing stroke so that once the pawl member passes the rack member, the surgeon will know that the jaw members are in the predetermined zone for releasing a partially closed clip. The rack member will ensure that the partial opening stroke which will release the partially closed clip will be terminated once the pawl member re-engages the rack member. The surgeon must then fully close the handle portion to reset the instrument to position a subsequent clip in the jaw mechanism for the next use.

It is also contemplated that the ratchet mechanism include a pair of rack members positioned in parallel relationship, where the first rack includes teeth over at least a partial closing distance and does not provide teeth for a portion of the closing stroke which will allow the surgeon to partially open the handle portion to release a partially closed clip positioned in the jaw mechanism. The second rack member, positioned next to the first rack member will include teeth over the distance in which the first rack member is devoid of teeth. Preferably, the teeth of the second rack member are spaced differently from the teeth of the first rack member so that the surgeon knows from the audible indication of the change in rack members that the jaw mechanism is in the predetermined zone for effecting a partial opening stroke of the handle portion to release the clip which is partially closed in the jaw mechanism. In this embodiment, one or two pawl members may be provided, or when a single pawl member is provided, a portion of the movable handle may engage the second rack member to provide the audible indication of the predetermined zone of the jaw mechanism.

The present invention also contemplates the provision of a visual indication for the surgeon, outside the patient's body, of the position of the jaw members, particularly when the jaw members are in the predetermined position or zone for partially closing a clip positioned between the jaw members. The visual indication may be provided on an instrument having the ratchet mechanism inside the handle. Moreover, the instrument may provide visible, audible and tactile indications of the position of the jaw mechanism. Within the handle portion, a first transmission means is provided for a linearly transferring motion from the movable handle to the clip advancing means, and a second transmission means for linearly transferring motion from the movable handle to the jaw closing means. The first transmission means which operates the clip advancement means comprises a pusher tube which is operatively connected to a pusher bar which extends the length of the instrument to push clips from the clip supply to the jaw mechanism. The second transmission means which operates the jaw closing means comprises a channel tube which is operatively connected to a sliding channel which extends the length of the body portion to effect opening and closing of the jaw members. In the preferred embodiment, an indicator or flag is provided on the channel tube which is visible through an aperture or window in the handle portion. When the instrument is at rest, such that the jaw members are fully opened to receive a clip therebetween, the flag on the channel tube is positioned within the handle away from the window or aperture. As the movable handle is moved through its closing stroke, the channel tube moves forward to urge the sliding channel forward to commence closing of the jaws and closure of a clip therebetween. Once the jaws have been closed a sufficient distance to effect a partial closure of the clip, the flag will appear in the aperture or window to indicate to the surgeon that a partial closure of the clip has been completed. At this point, the surgeon may commence a partial opening stroke of the handle portion to partially open the jaw mechanism to release the clip from between the jaw members. The visual indication may be used in conjunction with the ratchet mechanism described above, such that when the pawl member disengages from the rack member the flag will appear in the window to give the surgeon a visual, audible and tactile indication of the position of the jaw mechanism.

In a further embodiment of the present invention, a clutch mechanism may be provided on the handle portion, in particular on the movable handle, which may be manually set to provide the surgeon with the jaw positioning feature. Preferably, a pivotable clutch block may be provided on the movable handle which is positionable between an armed and a disarmed position. In the disarmed position, the clutch block is hidden within the structure of the movable handle, and may be pivoted to the armed position when the surgeon desires to utilize the jaw positioning feature. Once pivoted to the armed position, the clutch block protrudes from the movable handle towards the stationary hand grip. As the surgeon begins the closing stroke, the movable handle moves towards the stationary hand grip and the jaw mechanism begins to close. Once the clutch block engages the stationary hand grip, the surgeon will no longer be able to close the two handles. At this point, the surgeon will know that the jaw members are positioned a distance corresponding to a partial closure of a clip positioned therebetween, and he will know that in order to release the clip from the jaw mechanism he must ease up on the force for closing the movable handle. As the surgeon eases the force, and a partial opening stroke is commenced, the clip is released from the jaw mechanism and the clutch block will automatically move from the armed position to the disarmed position, thus allowing the surgeon to complete the closing stroke. As stated with the embodiments described above, this clutch block feature may be utilized with the internal ratchet mechanism within the handle and/or the flag mechanism associated with the channel tube. Accordingly, the surgeon may have a visual, audible and/or tactile indication of the position of the jaw members during the surgical procedure.

In an additional embodiment, an audible indicator in the form of a beeper may be provided to indicate the positioning of the jaw members with respect to the predetermined zone for partially crimping a clip. The stationary hand grip houses a small power cell such as a battery and the beeper itself. In addition, a small switch having a spring metal contact arm is provided to close the circuit and activate the beeper. As the pivoting handle is moved in the closing stroke, the beeper will sound when the jaws have been closed a sufficient distance to partially close the clip. The partial opening stroke will be completed when the beeper shuts off, indicating to the surgeon that the partially closed clip has been released and the complete closing stroke may be effected. It is also contemplated that a light or LED be provided in place of the beeper, although both the light and beeper may be provided together, providing the surgeon with the visible and audible indication of the jaw position.

An additional feature of the present invention is the provision of a novel rotation collar which allows for facile rotation of the body portion and jaw mechanism during use of the instrument. As the surgeon grips the handle potion of the instrument, he may rotate the body portion using his index finger to move the rotation collar which couples the body portion to the handle potion. The rotation collar of the present invention includes an external surface having a plurality of scalloped portions into which the fingertip of the surgeon's index finger may comfortably fit. In particular, the scalloped potions are dimensioned and configured to accept the volar surface, or fingerprint potion, of the distalmost phalange of the surgeon's index finger. The raised walls of the individual scalloped portions provide comfortable seating for the tip of the finger of the surgeon to prevent slipping during rotation of the collar.

The instrument of the present invention also includes a number of novel features which are associated with the jaw mechanism of the instrument. In particular, typical jaw mechanisms for surgical clip appliers provide a pair of jaw members which are machined from a single sheet of material and then secured to the distal end of the body portion of the instrument so that the jaw members may be flexed toward one another during closure of the instrument. The present invention provides a novel construction for the jaw mechanism in which the jaw members are constructed separately in mirror image so that the jaw members each include a clip crimping region and a mounting region. At the mounting region, there is provided a dovetail connection assembly to join the two jaw members together and a mounting means is also provided which includes a spacing between several of the dovetail joints which provides for mounting to the body potion of the instrument. Construction of the jaw members in accordance with this dovetail mounting feature allows the jaw members to be fabricated in simpler, more cost efficient manners, which eliminates the expensive machining process and increases the precision with which these jaw members are fabricated.

The present invention also provides, adjacent the jaw mechanism, a tissue stop which will contact a vessel or duct in the event the clip is not positioned in the jaw mechanism. The tissue stop of the present invention also includes a clip stop provision which will arrest the forward advancement of the clip into the jaw mechanism by the clip advancement means to prevent a clip from being pushed too far into and through the jaw mechanism. The clip stop means may comprise a tab member which extends upwardly to engage an inside surface of the clip, or may also comprise, in an alternate embodiment, a raised wall which engages at least the inside surface of the clip member as it is inserted into the jaws.

The present invention also provides a means for preventing splaying or over-opening of the jaw members, e.g., in the event that a clip is applied over a previously applied clip at the surgical site. The present invention provides a jaw stop mechanism which prevents the jaws from opening further than the at rest gap between the jaw members prior to the receipt of a clip. The jaw stop may comprise a bracket which surrounds the jaw members, or preferably, comprises a bracket having a pair of upstanding tabs which extend from the tissue stop member and engage into recesses provided in the jaw members to prevent the unwanted outward splaying of the jaws.

The jaw members of the present invention also include a clip blocking means which prevents the advancement of a clip into the jaw mechanism in the event the jaws are not fully opened in the clip receiving position. The present invention provides the crimping region with a blocking wall which prevents advancement of a clip by engaging the leg portions of the clip in the event the jaws are not opened to their clip receiving position.

The present invention also provides a means for accurately guiding a clip into the jaw mechanism from the clip supply. The clip advancing means in the present invention comprises a pusher bar which includes a cradling mechanism for holding and guiding a clip as it moves from the clip supply to the jaw mechanism. The cradling means engages at least an outside surface of the bight portion of the clip, which is the portion of the clip between the two legs. In one embodiment, the cradling means comprises a notch in the pusher bar whereby the pusher bar rides over the clip until the bight portion of the clip is engaged in the notch. Preferably, the notch includes a ramped forward portion which allows the pusher bar to move rearwardly off the clip so that the clip remains in the jaws after the pusher bar is retracted. In a second embodiment, the distalmost end of the pusher bar is provided with clip engaging fingers which may be integral with the pusher bar or which may be provided as a snap-on piece which will grasp and hold the clip as it is guided from the clip supply to the jaw mechanism. In a further embodiment, a single finger may pass over the bight portion of the clip, and since it is attached to or integral with the distalmost end of the pusher bar, guide the clip from the clip supply to the jaw mechanism.

BRIEF DESCRIPTION OF THE DRAWINGS

The foregoing features and further features of the present invention will become more readily apparent and may be understood by referring to the following detailed description of an illustrative embodiment of the clip applying instrument, taken in conjunction with the accompanying drawings, in which:

FIG. 2b illustrates an exploded perspective view of the body portion and jaw mechanism of the instrument of FIG. 1;

FIG. 3 illustrates a side plan view in partial cutaway of the handle of the instrument of FIG. 1 in its initial, or at-rest, position;

FIGS. 12a and 12b illustrate the jaw mechanism of the present invention;

DETAILED DESCRIPTION OF THE PREFERRED EMBODIMENTS

Figure 1:
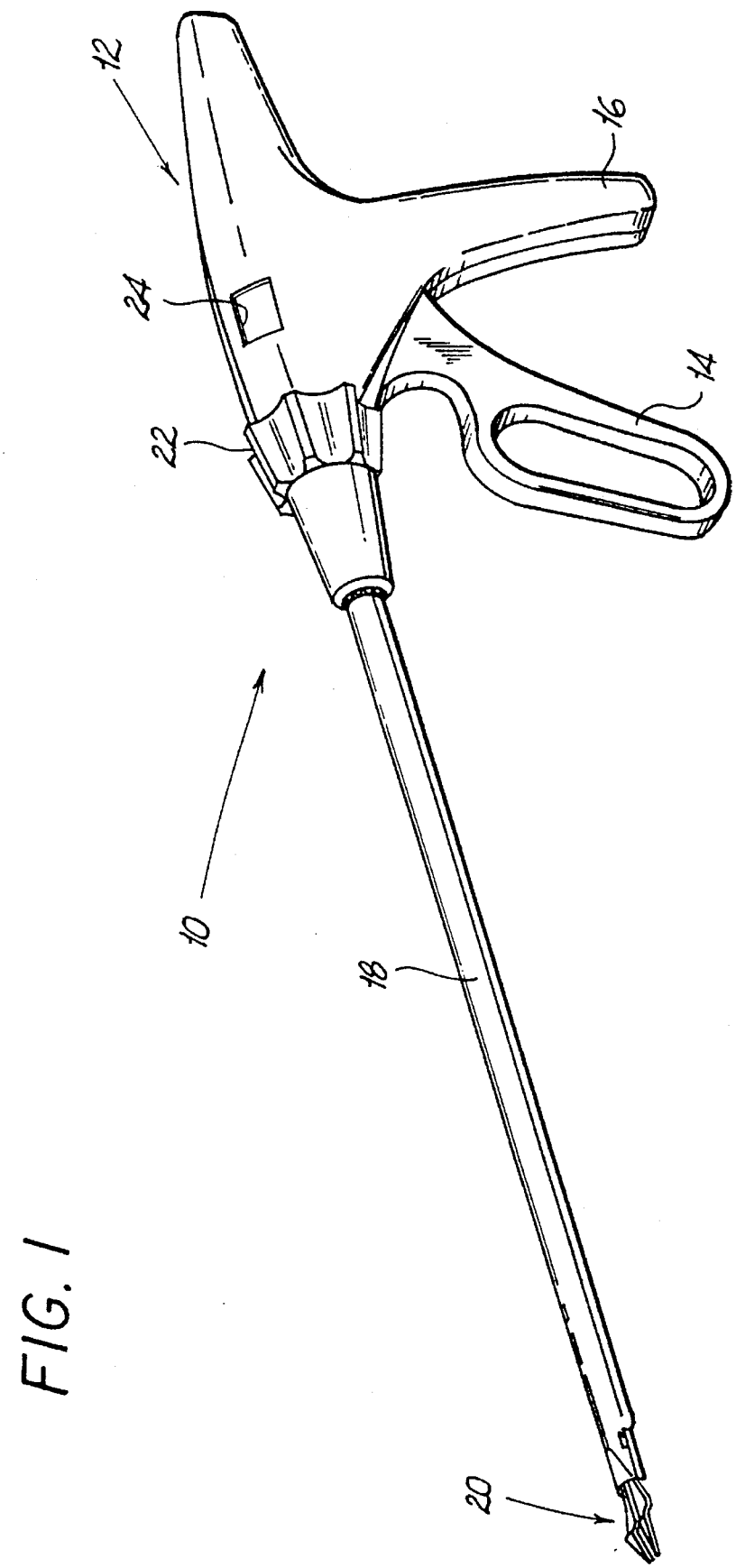
FIG. 1 illustrates a perspective view of the clip applying instrument of the present invention.

Referring now in specific detail to the drawings, in which like reference numerals identify similar or identical elements throughout the views, FIG. 1 illustrates the clip applying instrument 10 of the present invention. Clip applying instrument 10 includes a handle portion 12 having a movable handle 14 and a stationary hand grip 16, which serves to operate a jaw mechanism 20 through the provision of an elongated body portion 18. The junction at which body portion 18 is joined to handle portion 12 includes a rotation collar 22 for varying the orientation of the jaw mechanism at the surgical site. Handle portion 12 further includes an aperture or window 24 which provides a visual indication of at least one position of the jaw members during a closing stroke of the handle portion. These elements will be described in detail below.

Figure 2A:
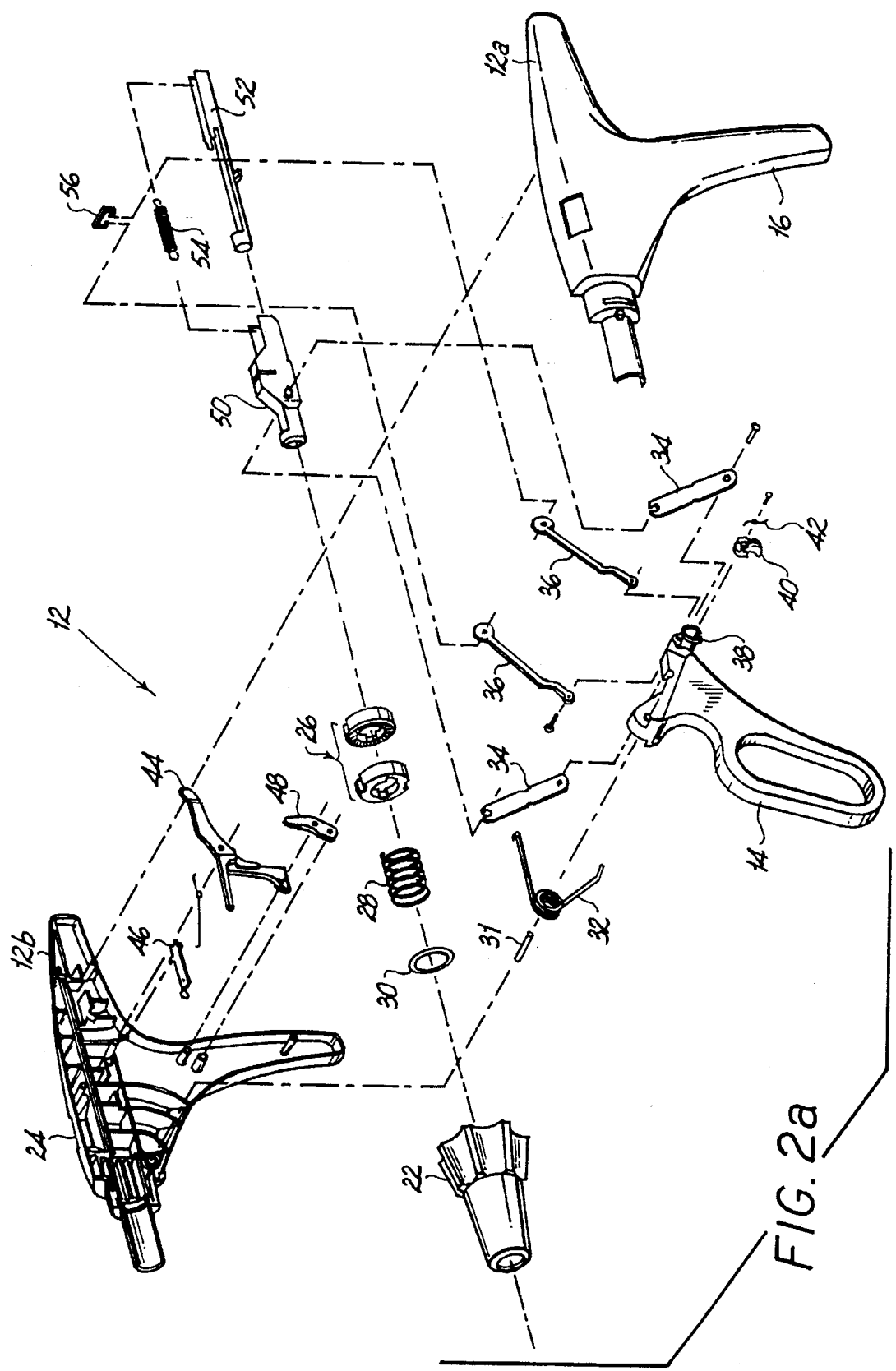
FIG. 2a illustrates an exploded perspective view of the handle portion of the instrument of FIG. 1.
Figure 26A:
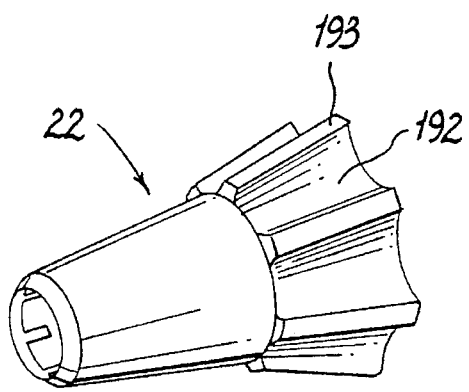
FIGS. 26a–26c illustrate the components of the rotation collar of the present invention.
Figure 26B:
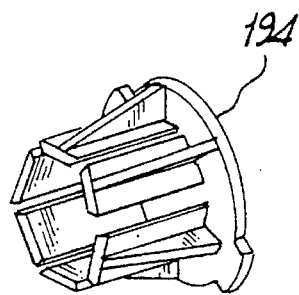
Figure 26C:
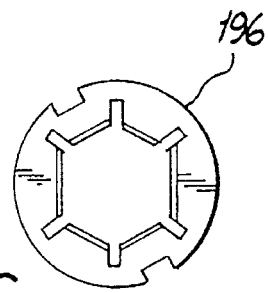
Figure 27:
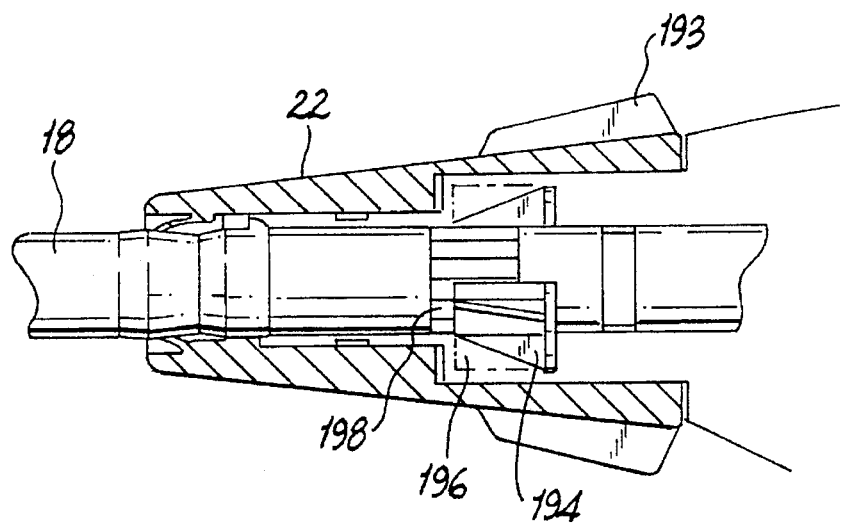
FIG. 27 illustrates a side cross-sectional view of the rotation collar of the present invention as it is positioned at the junction of the body portion and the handle portion.

FIG. 2a illustrates the components of the handle portion 12 of instrument 10 of FIG. 1. The handle portion 12 includes a housing 12a and 12b within which the components of the handle portion are positioned. Rotation collar 22 includes a rotation ratchet mechanism 26 which provides for incremental rotation of rotation collar 22. A biasing spring 28 and a washer assembly 30 are provided to apply pressure to the ratchet mechanism 26. Rotation collar 22 is further described in detail with respect to the preferred embodiment of the rotation collar 22 as illustrated in FIGS. 26 and 27 below.

Movable handle 14 is secured to the housing halves by a pin 31 which permits rotation of movable handle 14 with respect to stationary hand grip 16. A handle spring 32 is provided to bias movable handle 14 to the open position, and movable handle 14 is connected through a series of linkages to effect loading of a clip into the jaw mechanism as well as crimping of a clip as will be described below. A pusher robe 52 and a channel tube 50 are provided in nested arrangement and are operatively connected to the movable handle 14 through channel robe links 34 and pusher tube links 36. A spring member 54 secures pusher robe 52 and channel robe 50 to each other, which are held in place by a C-clamp 56.

Movable handle 14 further includes a pawl member 40 which is secured with a pawl spring 42 to the pawl housing 38 which is pan of movable handle 14. As will be described below, pawl member 40 engages rack member 48 to provide for incremental closure of the movable handle 14, which in turn effects incremental closure of the jaw mechanism at the distal end of the instrument. A lever 44 is provided along with a latch plate 46 to coordinate the movements of pusher tube 52 and channel tube 50 with respect to the movable handle 14.

As will be described below, channel tube 50 is operatively connected to a camming mechanism which includes a slidable channel to effect camming or closing of the jaw members to crimp a clip therebetween. Pusher tube 52 is operatively connected to a pusher bar mechanism which serves as the clip advancement means to advance a clip from the clip supply to the jaw mechanism. The operation of the handle mechanism with respect to the jaw mechanism will be discussed below.

FIG. 2b illustrates the body portion 18 and jaw mechanism 20 of the instrument 10 of FIG. 1. Body portion 18 includes an upper housing half 58 and a lower housing half 86, within which are enclosed the operative elements of the body portion for advancing a clip to the jaw mechanism and for camming the jaw members closed to crimp a clip positioned therebetween. A pusher bar 60 is provided which is operatively connected at handle engagement means 85 to the pusher tube 52 illustrated in FIG. 2a. A clip feed spring 62 is provided for urging individual clips from the clip supply 70 through the provision of pin holder 66 and clip follower 68. A seal block 69 is provided toward the proximal end of upper housing half 58 and lower housing half 86 to obstruct the passage of gaseous media therethrough. Sealing block 69 preferably receives a sealing material, e.g., silicone grease, to improve its sealing function. As is known in the art, when all the clips have been delivered, clip follower 68 prevents further advancement of pusher bar 60 to give an indication to the surgeon that the instrument is no longer operative and has been emptied of its clips. A cover plate 72 is also provided to overlay the jaw mechanism 20 when the instrument is assembled to facilitate crimping of a clip positioned between the jaws.

Jaw mechanism 20, which will be described in detail below, includes the jaw members 75, a tissue stop 78, a channel slide plate 80, and a camming channel 82 which is operatively connected at the handle engagement means 84 to the channel tube 50 discussed above with respect to FIG. 2a. A crimping bracket 76 is spot welded to the distal end of camming channel 82 to assist the camming of the jaw members 75 towards each other to crimp a clip positioned therebetween. The entire body portion is secured together with the assistance of C-clamp 88.

Turning now to FIG. 3, the operation of the handle mechanism of the instrument 10 will be described. FIG. 3 shows the instrument 10 in its initial position prior to the advancement of a clip to the jaw mechanism 20. As can be seen in FIG. 3, the jaw mechanism is in its initial at-rest position in which the jaw members 75 are separated an initial distance $D_1$ where the jaw members 75 are in their clip receiving position. Pusher bar 60 is in its retracted position out of the vicinity of the jaw members 7 5, and behind a clip in anticipation of feeding the clip to the jaw mechanism 20. As can be seen in FIG. 3, pusher tube 52 is in its fully retracted position awaiting slight movement of movable handle 14 to feed a clip to the jaw mechanism 20. Pusher tube 52 is held in the position shown in FIG. 3 by pusher tube lever 44 which is engaged in a slot 53 in pusher tube 52. Lever 44 is maintained in this position until movable handle 14 is moved slightly in the direction of stationary hand grip 16 so that detent 90 on lever 44 engages a corresponding detent on an end of handle 14 to effect a slight pivoting motion of lever 44 out of slot 53, to permit advancement of pusher tube 52 under the influence of pusher tube spring 54 to the position shown in FIG. 4. As seen in Pig. 4, movable handle 14 is still substantially in the at-rest position, and in fact handle pawl member 40 has not yet engaged rack member 48. In this position, pusher tube 52 is fully advanced, thus moving the pusher bar 60 in a distal direction to advance a clip 144 to the jaw mechanism 20.

Figure 5:
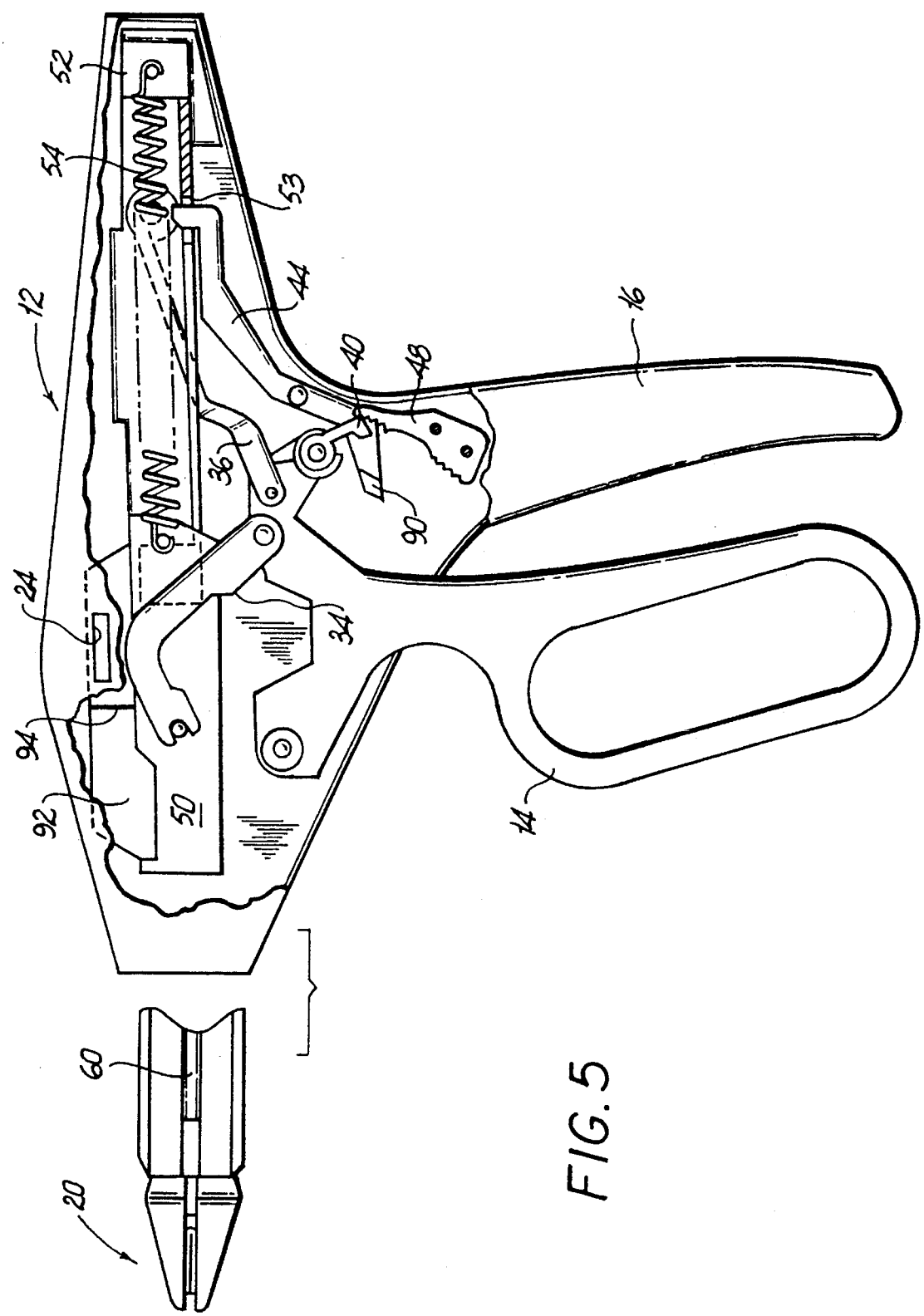
FIG. 5 illustrates a side plan view in partial cutaway of the handle of the instrument of FIG. 1 in the clip crimping position.
Figure 6:
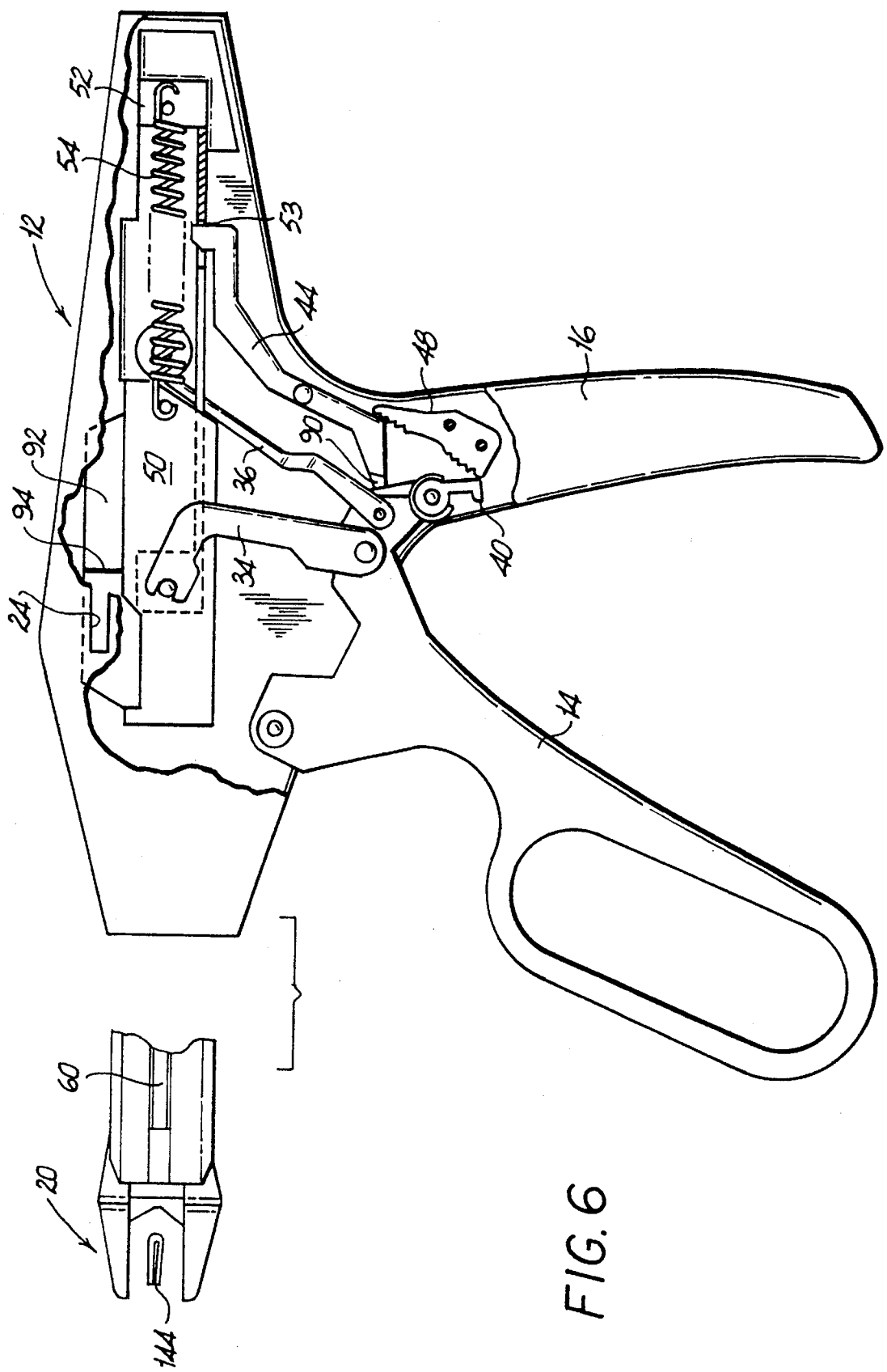
FIG. 6 illustrates a side plan view in partial cutaway of the handle of the instrument of FIG. 1 in the at-rest position after crimping of a clip and prior to subsequent feeding of a successive clip.

As seen in FIG. 5, as a full closing stroke of movable handle 14 is effected towards stationary hand grip 16, channel tube 50 is advanced through the provision of channel tube link 34, while pusher tube link 36 simultaneously moves pusher tube 52 in the direction towards the proximal end of the handle portion 12. In the position shown in FIG. 5, channel tube 50 is fully advanced, thus moving camming channel 82 fully forward to cam the jaw members 75 closed to crimp clip 144 positioned therebetween. Since pusher tube 52 is moved to its proximalmost position, it has consequently withdrawn pusher bar 60 out of the jaw mechanism to the clip supply 70 to be in position to feed a subsequent clip to the jaw mechanism 20. However, as pusher robe 52 is moved to the position shown in FIG. 5, lever 44 is pivoted back into slot 53 to maintain pusher tube 52 in the position shown in FIG. 5. As the movable handle 14 returns to its fully open position, as seen in FIG. 6, channel tube 50 returns to its initial position under the influence of channel robe link 34, while pusher robe 52 is maintained in a proximal position due to lever 44. In this position, as seen in FIG. 6, the pusher bar 60 has not yet been advanced so that the jaws 75 are empty, awaiting a slight closing stroke of movable handle 14 to feed the next clip to the jaw mechanism 20.

Having thus described the operation of the internal components of the handle portion 12, reference will be made to FIGS. 7 and 8 which illustrate the partial crimping feature of the present invention. As discussed previously, it is often times desirable to provide a means for applying a partially closed clip during certain surgical procedures, in particular during a cholecystectomy procedure, more commonly known as gall bladder surgery. In such a procedure, it is sometimes necessary to place a shunt or robe into a duct to introduce media to the duct, while at the same time maintaining the shunt in place. Accordingly, it becomes necessary to secure the shunt in place through the application of a clip, but it is necessary to prevent occlusion of the shunt through the provision of a partially closed clip. Furthermore, since the cholecystectomy procedure has now gained increased popularity as an endoscopic procedure, the surgeon's reliance on the endoscope to determine when a clip has been partially crimped introduces additional challenges. Although the surgical site is viewed on a video monitor, the field is somewhat distorted and it may be difficult to accurately determine when the clip is partially crimped about the duct or shunt. In addition, the closing mechanism for the instrument must ensure that the partially closed clip does not disengage from the instrument prior to securement on the duct or shunt.

Figure 4:
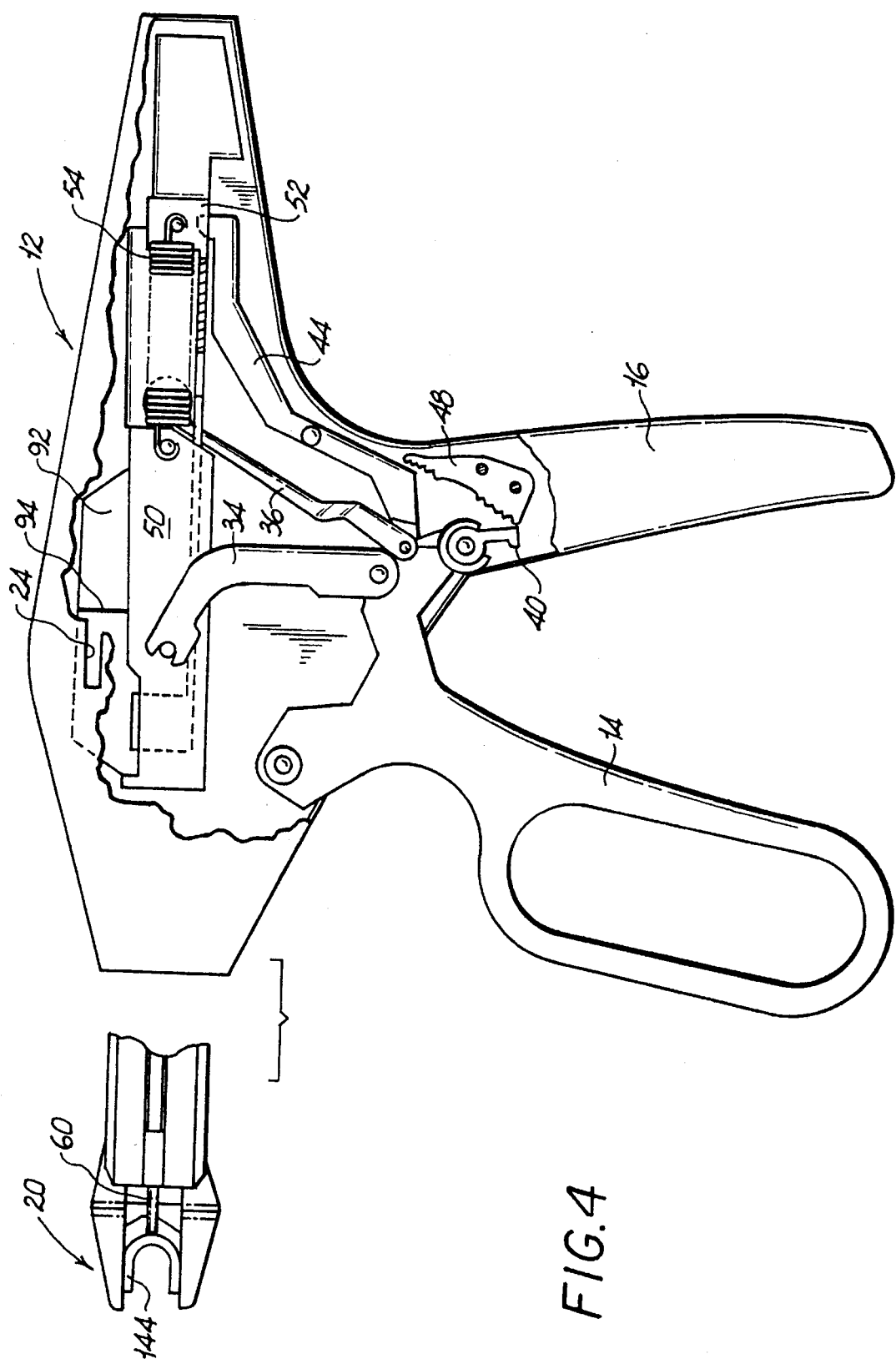
FIG. 4 illustrates a side plan view in partial cutaway of the handle of FIG. 3 in a position in which a clip is loaded into the jaw mechanism.
Figure 7:
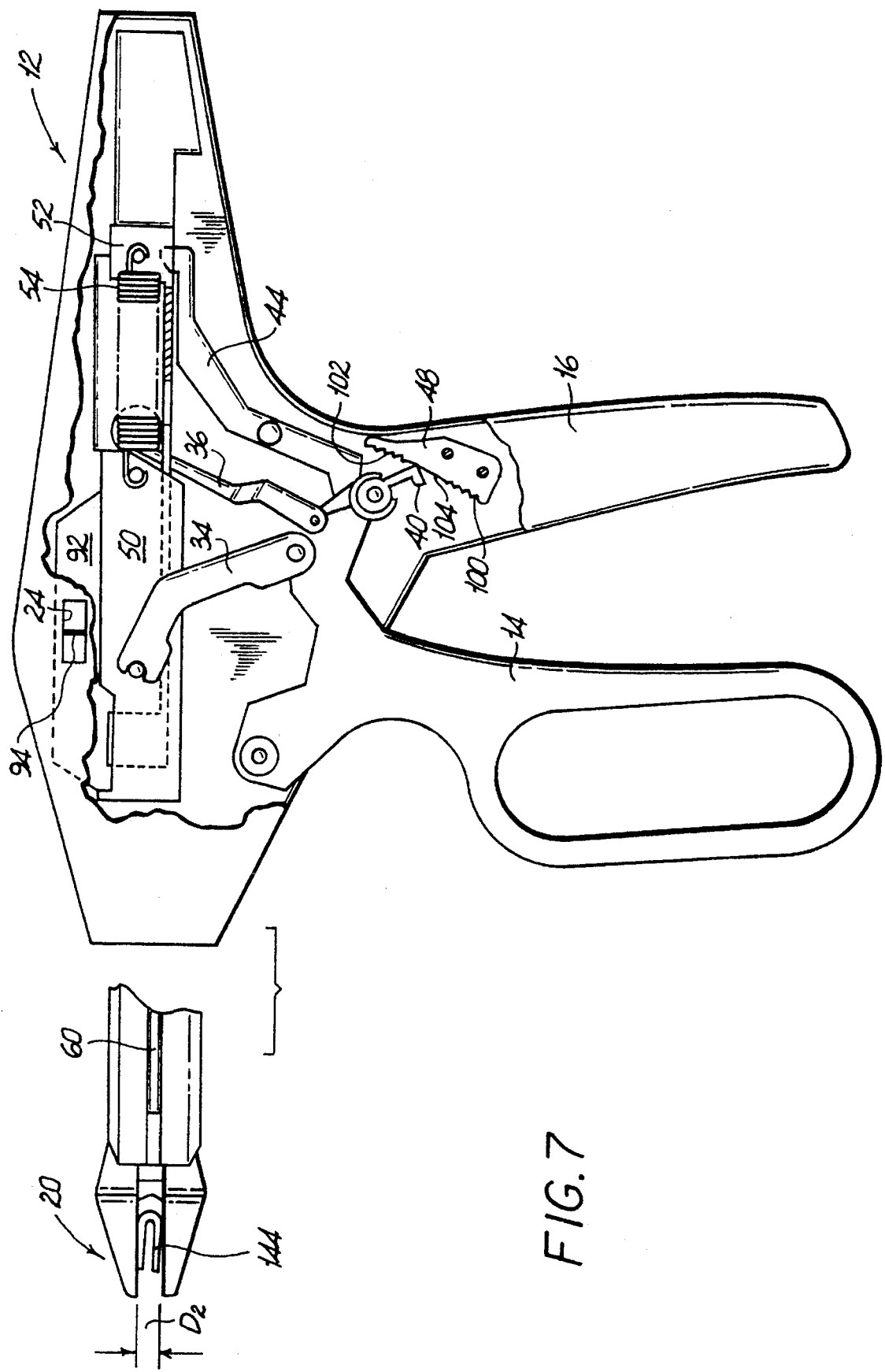
FIG. 7 illustrates a side plan view in partial cutaway of the handle of the instrument of FIG. 1 in which the jaw mechanism is in a predetermined position indicative of a partial closing stroke to partially crimp a clip positioned in the jaws.
Figure 8:
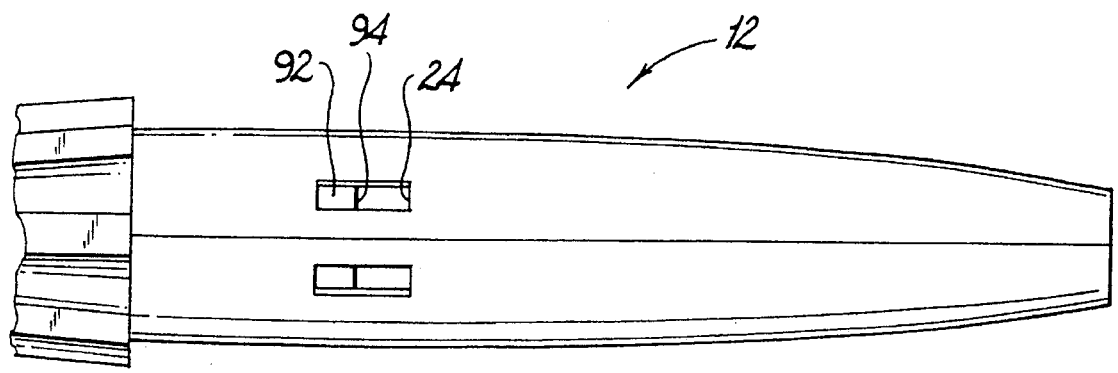
FIG. 8 illustrates a top plan view of the handle of the instrument of FIG. 1 showing the visual indication of the predetermined position of the jaw mechanism of the embodiment of FIG. 7.
Figure 9:
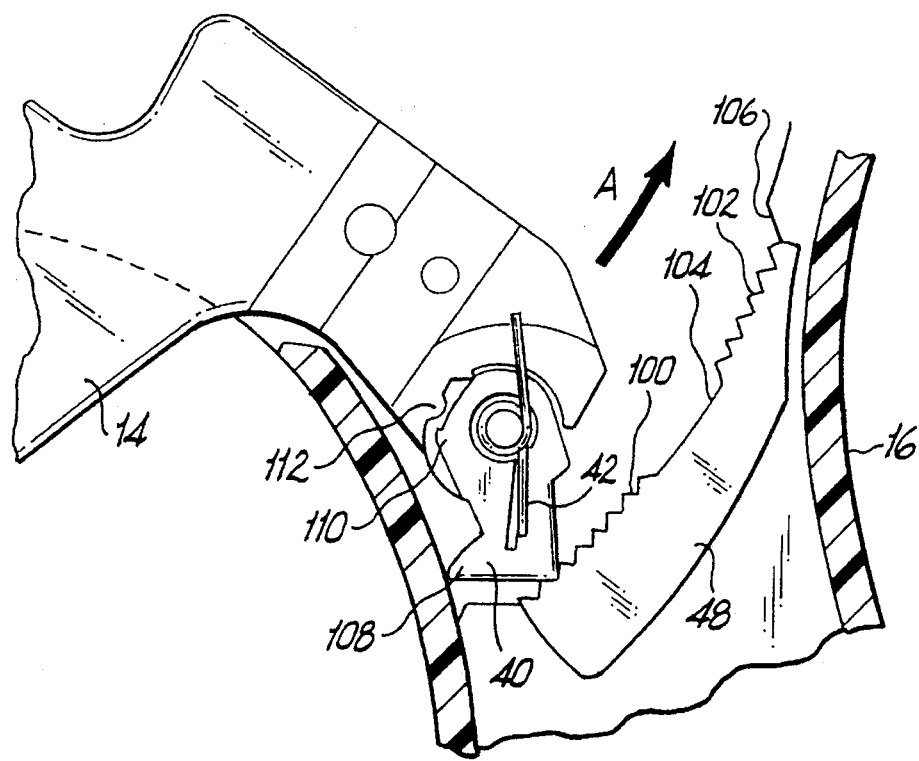
FIG. 9 illustrates the ratchet mechanism of the present invention during a closing stroke of the handle mechanism.
Figure 10:
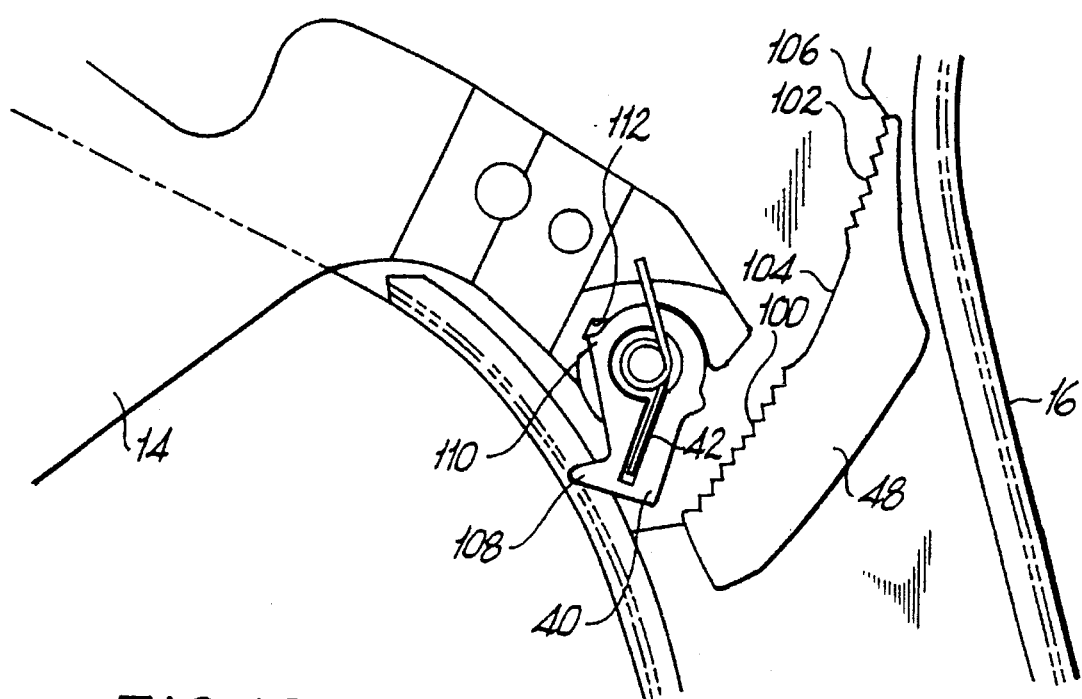
FIG. 10 illustrates the ratchet mechanism of the present invention during an opening stroke of the handle mechanism.

Turning now to FIG. 7, and with particular reference to FIGS. 9 and 10, there is illustrated the mechanism of the present invention which provides for a partial closure of a clip for application to tissue, in particular a duct within the body to secure the duct or to place a shunt in the duct during the surgical procedure. The mechanism of the present invention allows the surgeon to know when the jaw members are at a predetermined position indicating a partial closure of the clip for proper securement on the shunt and/or duct. Reference is also made to FIGS. 3–6 disclosed above. After a clip has been fed to the jaw mechanism, the instrument is in the position as shown in FIG. 4 above. In this position, the jaw members 75 are separated by an initial distance $D_1$ which indicates the clip receiving position of the jaw mechanism 20. As the movable handle 14 is moved towards the stationary hand grip 16, the pawl member 40 engages rack member 48 to provide for incremental closure of the handle mechanism, and consequently the jaw mechanism 20 as the surgeon continuously moves handle member 14 towards stationary hand grip 16. As seen in FIG. 9, the rack member allows for a closing stroke as pawl member 40 passes over teeth 100 of rack member 48. The teeth 100 prevent movement of the handle in the opening direction, or away from stationary hand grip 16. As the pawl member 40 is moved over teeth 100 in the direction of arrow A, the jaw mechanism slowly closes to crimp the clip 144 that is positioned between jaw members. As pawl member 40 passes over teeth 100, the surgeon is provided with a tactile indication of the position of the jaw mechanism by feeling the clicks of the pawl member 40 over the teeth 100. The clicking also provides an audible indication of the position of the jaw members as they begin the crimping of the clip.

Once the pawl member 40 reaches the position shown in FIG. 7, such that the pawl member 40 is positioned over the space 104 between the first teeth 100 and the second teeth 102, the surgeon will know through the tactile indication of the cessation of the clicking of the pawl member 40 over the teeth 100, as well as the cessation of the audible clicking sound, that the jaw members are in the predetermined position having the distance $D_2$ between them corresponding to a partial crimping of the clip. When the pawl member 40 is positioned over space 104, the surgeon may effect a partial opening stroke of the handle member which will permit the clip 144 to be disengaged from the jaw mechanism 20. The opening stroke will of course be regulated by the distance of the space 104, since once the pawl member 40 re-engages the teeth 100, the opening stroke will no longer be permitted. After the clip has been released from the jaw mechanism in a partially closed manner over the duct, or the shunt that is positioned in the duct, the instrument must be reset to allow subsequent clip applications by completing the closing stroke so that the pawl member 40 passes through the space 104 and completely over the second set of teeth 102.

Once the closing stroke is completed, teeth 102 still prevent pawl member 40 from traveling in a direction opposite arrow A, thus preventing an opening stroke of the movable handle 14. Accordingly, upon fully closing movable handle 14 to stationary hand grip 16, pawl member 40 engages blocking wall 106, which causes pawl member 40 to rotate in a clockwise direction with respect to FIG. 9. Rotation in the clockwise direction moves pawl detent 110 over handle detent 112 to the position shown in FIG. 10. When pawl detent 110 is in the position shown in FIG. 10 with respect to handle detent 112, the pawl member 40 is held in a position that fully disengages pawl member 40 from rack member 48. This allows an opening stroke of the handle mechanism so that the handle may return to the position shown in FIG. 6 to await feeding and application of the next clip. Referring once again to FIG. 10, as the handle mechanism fully opens, boot portion 108 of pawl member 40 will engage the wall of stationary hand grip 16, which causes pawl member 40 to rotate in a counter-clockwise direction with respect to FIG. 10, thus moving the pawl detent 110 back over handle detent 112 to return the pawl member 40 to the position shown in FIG. 9. The handle is once again ready to be used to apply a subsequent clip.

Having described the audible and tactile indicators which allow the surgeon to determine when the jaw mechanism is in the predetermined position $D_2$ for the application of a partially closed clip, reference is once again made to FIG. 7, along with FIG. 8, so that the visual indicator may now be described. As seen in FIGS. 7 and 8, the present invention provides a window 24, preferably on either side of handle portion 12, which provides for a visual indication of the spacing between the jaws so the surgeon knows when the jaw members are in the predetermined position $D_2$ for the application of a partially closed clip. As can be seen in FIG. 7, channel tube 50 includes a shroud portion 92 upon which is positioned a flag 94. As the handle member 14 is moved towards stationary hand grip 16, as described above, channel tube 50 moves in the direction towards the distal end of the instrument through the provision of channel tube link 34. As the handle is closed, channel tube 50 moves forward with flag 94 appearing in the window 24 of the handle 12. Once the flag 94 is visible in the indicator window 24, the surgeon knows that jaw members 75 have been sufficiently closed to partially crimp a clip 144 positioned therebetween. It is contemplated that the visual indicator flag 94 may be utilized with the audible and tactile indicators comprising the ratchet mechanism in the handle 12 described above. Once the surgeon sees the flag 94 in the window 24, he will know that the jaws are in the predetermined position $D_2$ and a partial opening stroke may be effected to release the partially closed clip 144 from the jaw mechanism 20. After the partially closed clip is released, the handle is fully closed to reset the instrument as described above. Of course, it is also contemplated that the visual indicator may be used by itself to provide the surgeon with a purely visual indication of the position of the jaw members.

Figure 24:
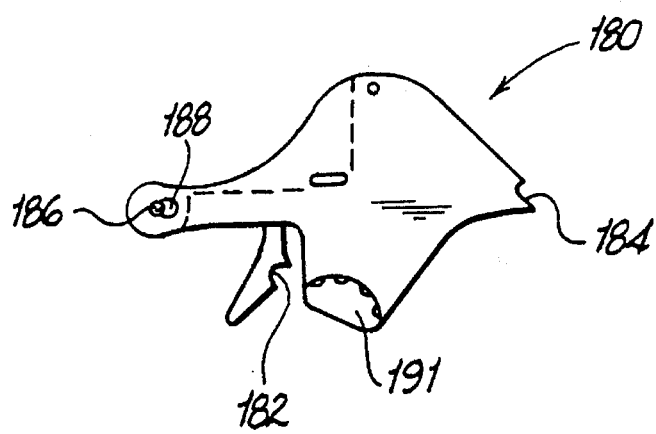
FIG. 24 illustrates a plan view of the handle block mechanism.
Figure 25A:
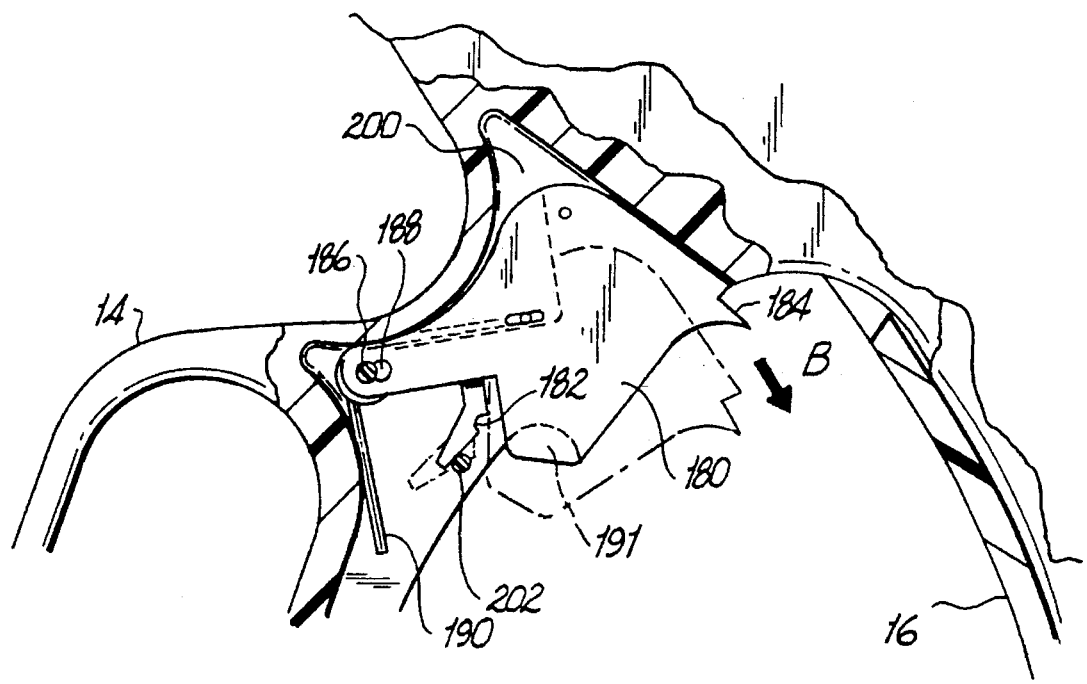
FIGS. 25a and 25b illustrate a side plan view in partial cutaway of the movable handle of the present invention employing the handle block member of FIG. 24.
Figure 25B:
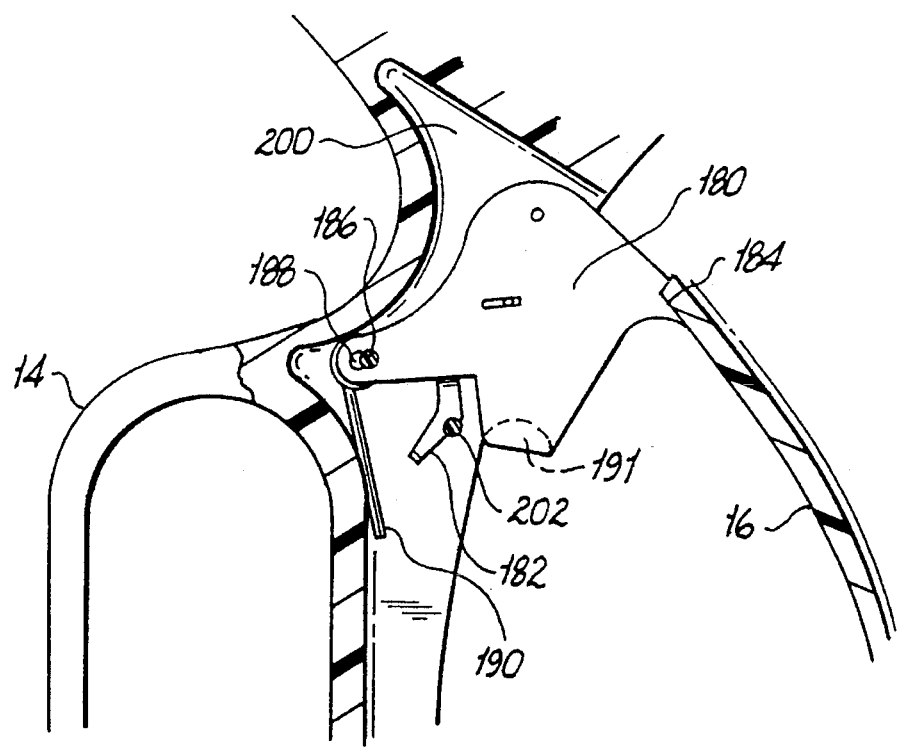

FIG. 24 and FIGS. 25a–25b illustrate a further mechanism for providing indication to the surgeon of the predetermined distance $D_2$ for the application of a partially closed clip. In FIG. 24, there is shown a handle block member 180 for positioning in movable handle 14 as seen in FIG. 25a. Block 180 includes a flexible notch lock 182 and a handle engagement notch 184. A pivot pin 186 is provided, along with an eccentric pin slot 188. The entire mechanism is biased by a spring member 190. Turning to FIG. 25a, the block 180 is stored in a recess 200 of handle member 14. Spring 190 maintains block 180 in the recess 200 until the surgeon desires to move the block 180 into an armed position. To do so, the surgeon moves block 180 through the provision of finger notch 191 in the direction of arrow B to an armed position where notch lock 182 engages pin 202. As the movable handle 14 is moved toward stationary hand grip 16, the handle engagement notch 184 contacts stationary hand grip 16 as shown in FIG. 25b. In this position, the handle has closed a sufficient distance to close the jaw mechanism to the predetermined position so that the distance between the jaw members is equal to $D_2$. In this position, the clip has been crimped sufficiently to partially close the clip about a duct or shunt. When the handle block 180 is in the position shown in FIG. 25b, it can be seen that pin slot 188 has shifted with respect to pin 186, and in order to release handle block 180, the surgeon partially opens the handle mechanism so that a partial opening stroke of handle 14 is commenced. In this position, spring 190 returns block 180 into the recess 200 so that the block 180 is in the position shown in FIG. 25a. The handle may then be fully closed to reset the instrument for application of a subsequent clip. As discussed above with the various indicator means, the handle block 180 may be utilized with the visual, audible, and tactile indicators as addressed above, or may be used by itself.

Figure 28:
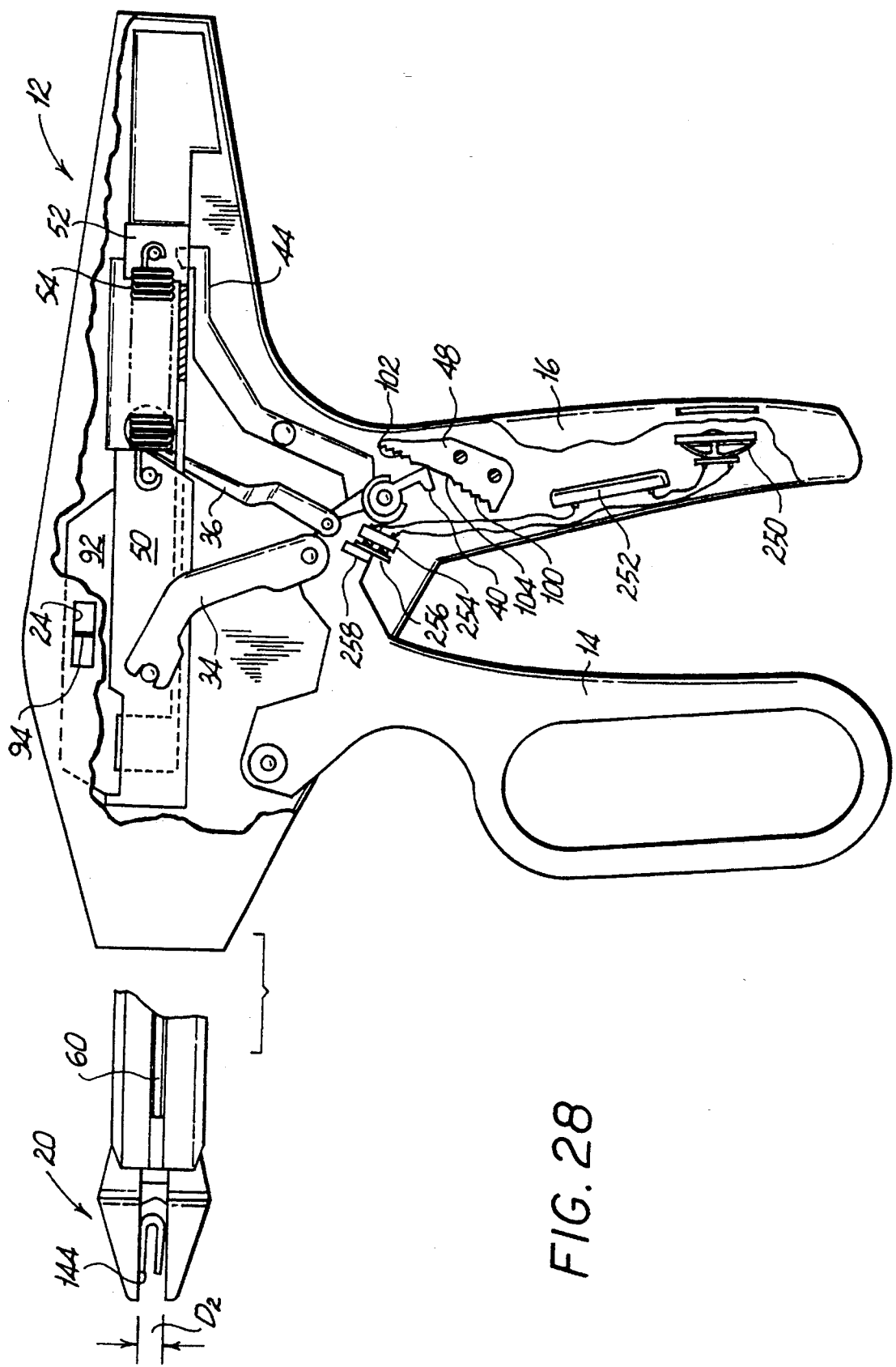
FIG. 28 illustrates a side plan view in cutaway of the handle mechanism of the present invention employing an audible indicator of the position of the jaw members in relation to a predetermined position.
Figure 29:
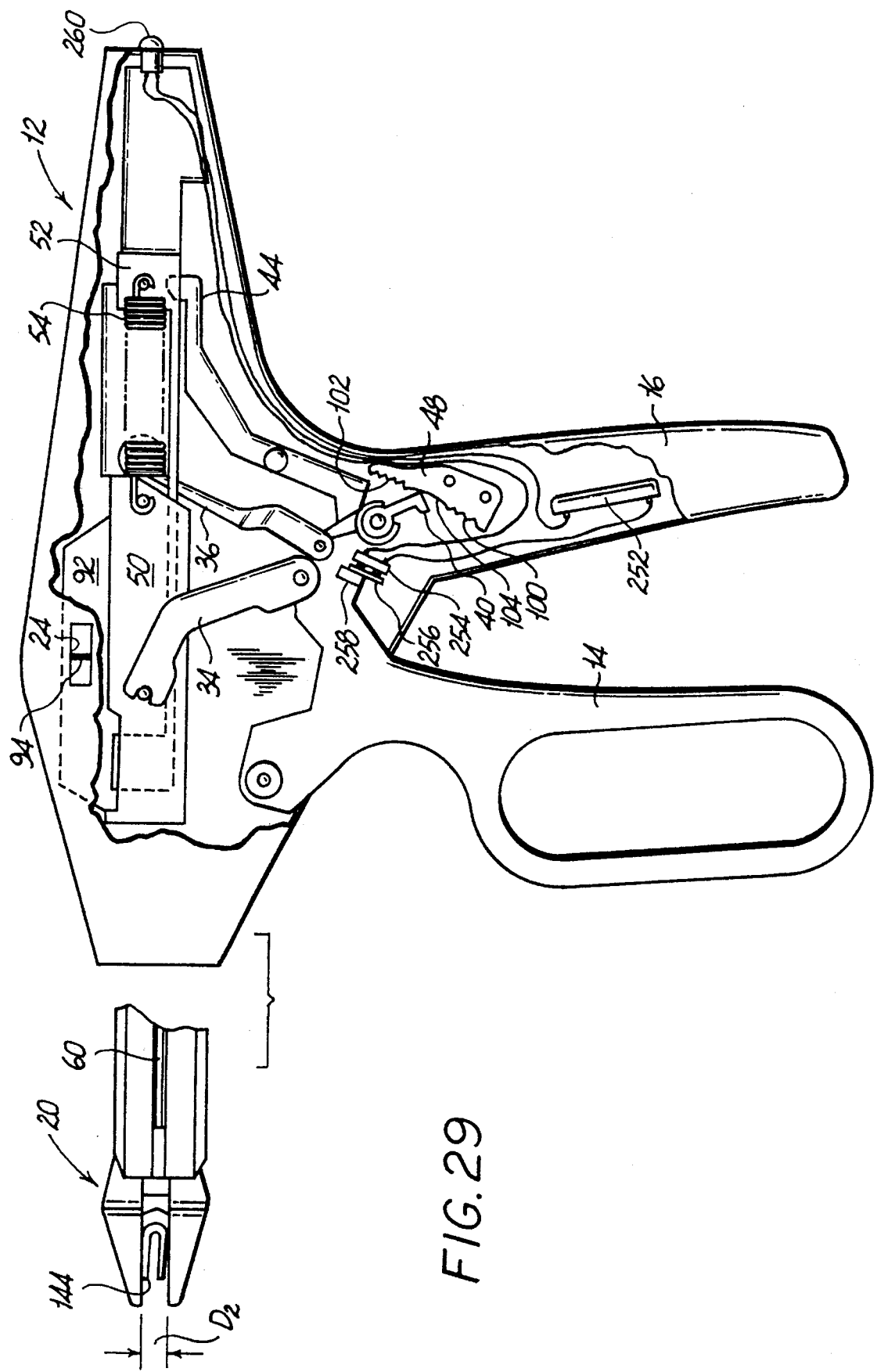
FIG. 29 illustrates a side plan view in cutaway of the handle of the present invention employing a visual indication of the position of the jaw members in relation to a predetermined position.

Turning now to FIGS. 28 and 29, alternate embodiments of the indicators are disclosed. In FIG. 28, an audible indicator comprising a small speaker or beeper 250 is provided in the stationary hand grip 16 and is associated with a battery pack 252 and a switch 254 having a spring contact arm 256 which is actuated by a shoulder 258 on the movable handle 14. As the handle is closed, and the jaw members reach the predetermined position $D_2$ indicative of a partially closed clip, the shoulder 258 on the movable handle 14 will have traveled to the position of engagement with the spring arm 256 of the switch 252 to close the switch contacts and cream an audible sound through the beeper 250. When the surgeon hears the beeper, the jaw members 75 will be in the predetermined position $D_2$ and the surgeon will know to begin the partial opening stroke to release the partially closed clip. The partial opening stroke will be terminated when the beeper shuts off. The partially closed clip is then released, and the full closing stroke may be completed to reset the instrument. It is contemplated that activation means, e.g., a toggle switch, may be associated with handle portion 12 to allow the surgeon to activate the electronic mechanism when it is desired to benefit from the audible indicator provided thereby.

With reference to FIG. 29, a similar arrangement is provided as that disclosed in FIG. 28. However, instead of a beeper 250, a small light bulb or LED 260 is provided within the handle 16 which will provide a visible indication of the position of the jaw mechanism with respect to the predetermined position $D_2$. In this embodiment, movement of the movable handle 14 towards the stationary handgrip 16 a sufficient distance will close the contacts of the switch 254 as the shoulder 258 of the movable handle 14 contacts the spring arm 256 of the switch 254. Once the contacts are closed, the light 260 will be illuminated, through the provision of the battery 252, and the surgeon will have a visual indication that the jaw mechanism is now in the predetermined position $D_2$ and that the partial opening stroke may be commenced to release the partially closed clip from the jaw mechanism. Of course, it is contemplated that the embodiment of FIG. 29 may be utilized by itself, or in combination with the embodiment of FIG. 28, or any of the other position indicator embodiments described above.

Figure 11A:
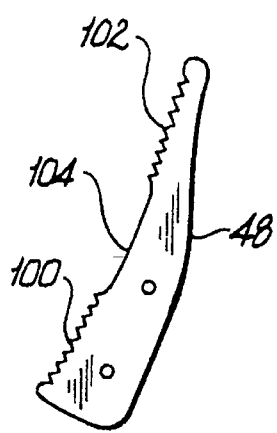
FIGS. 11a–11d illustrate the rack member of the ratchet mechanism of the present invention.
Figure 11B:
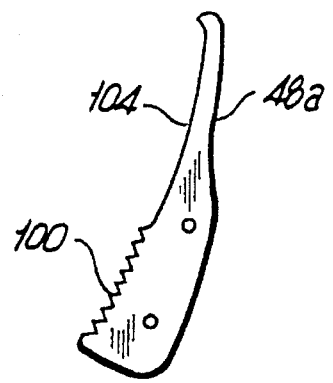
Figure 11C:
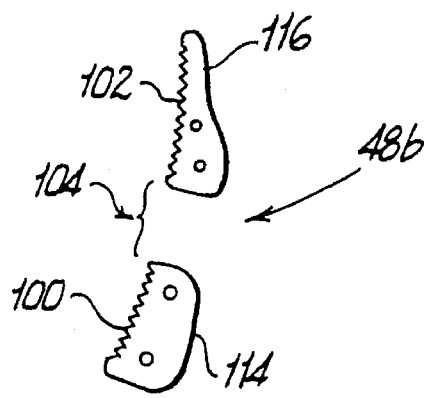
Figure 11D:
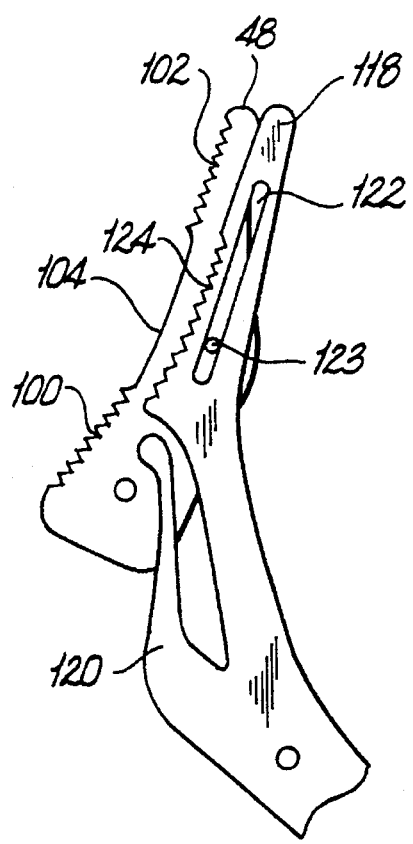

FIGS. 11a–11d illustrate various embodiments of the rack member 48. Since it is desirable to ensure a partial closing stroke prior to the partial opening stroke to release the partially crimped clip, the first set of teeth 100 are provided to ensure the partial closing stroke as the pawl member 40 moves across rack member 48. As seen in FIG. 11a, the embodiment disclosed above, once the partial closing stroke is completed as the pawl member 40 passes over teeth 100, the space 104 provides a means for effecting the partial opening stroke to allow the partially closed clip to be released from the jaw mechanism. After release of the clip, teeth 100 prevent further opening of the handle mechanism, and requires the surgeon to fully close the instrument by ensuring that the pawl member 40 passes over second set of teeth 102. FIG. 11b illustrates an alternate embodiment of the rack member 48, and illustrates rack member 48a which includes teeth 100 and an elongate space 104. After the pawl member 40 passes over teeth 100, the opening stroke may be effected anywhere within space 104. After the clip that is partially closed has been released from the jaw mechanism 20, the surgeon fully completes the closing stroke as the pawl member 40 passes over the space 104. Teeth 100 prevent a full opening stroke without the full closing stroke. FIG. 11c illustrates a further embodiment of rack member 48b where two rack members are positioned in series relation with respect to each other and the space 104 is actually the area between the two separate rack members 114 and 116. Rack 114 includes the first set of teeth 100 and rack 116 includes the second set of teeth 102. Once the partial closing stroke is completed as the pawl member 40 passes over teeth 100, the surgeon may effect the partial opening stroke as the pawl member 40 is positioned at the location of the space 104 between the two rack members. The partial opening stroke will be completed when the pawl member 40 re-engages teeth 100, and the surgeon must fully close the handle by passing pawl member 40 over teeth 102 to return the instrument to the set position for further use. FIG. 11d illustrates a further embodiment of the rack mechanism of the present invention. Rack member 48 is provided with a parallel rack 118 which is positioned in parallel relationship. Rack member 118 includes a plurality of teeth 124 which are positioned adjacent space 104. It is contemplated in this arrangement that parallel rack 118 includes spring arm 120 which provides for flexible movement of parallel rack 118 at its connection point 123 with rack 48. As the handle mechanism is moved in a closing stroke, pawl member 40 passes over teeth 100 to ensure the partial closing stroke. As pawl member 40 passes into space 104, a shoulder portion of the movable handle 14 (not shown), or a second pawl member (not shown) may engage teeth 124 to provide the surgeon with a tactile or audible indication that the jaw mechanism is in the predetermined position $D_2$. It is contemplated that the teeth 124 provide a different feel and different sound than that associated with the teeth 100 and 102 of rack 48. In addition, the flexibility of parallel rack 118 due to the spring arm 120 will provide the surgeon with a different feel to indicate that the jaw mechanism 20 is in the predetermined position $D_2$.

Turning now to FIG. 12, there is illustrated the novel jaw mechanism of the present invention. Typically, jaw mechanisms are constructed from a single sheet of material in which the jaw structure is machined in an expensive and time-consuming process to form the individual jaw members 75. The present invention provides a pair of jaw members 126 and 128 which are constructed in mirror image and include a crimping region 130 and a mounting region 134. The individual jaw members 126 and 128 are secured together by a dovetail connection arrangement 132 which secures the two jaw members together and provide a mounting means 136 through the provision of spaces between the dove-tail portions. The present invention provides a simple and cost efficient means for constructing the jaw mechanism which is assembled prior to assembly on the instrument itself.

Figure 13A:
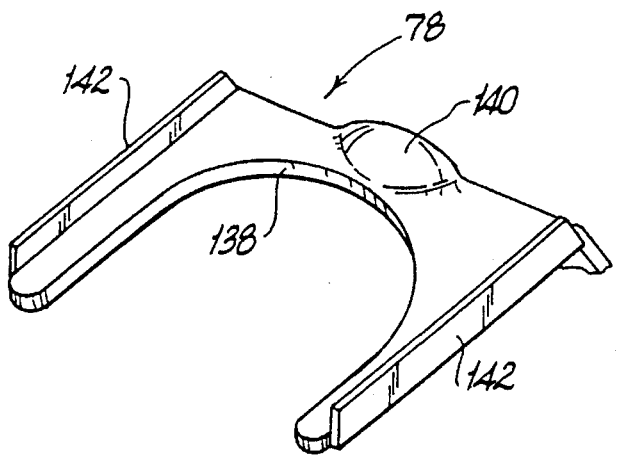
FIGS. 13a–13c illustrate a first embodiment of the tissue stop of the present invention having a clip stop member and a jaw stop member positioned thereon.
Figure 13B:
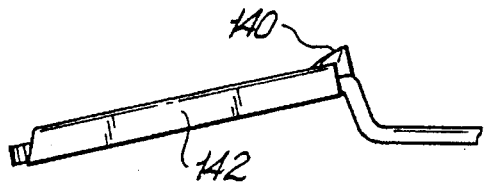
Figure 13C:
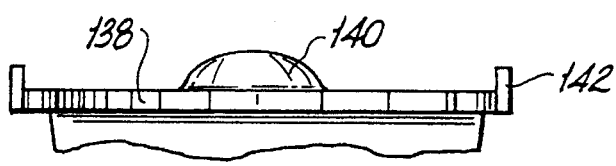

Turning now to FIG. 13, there is illustrated the novel tissue stop 78 of the present invention. FIGS. 13–17 illustrate various embodiments of the tissue stop, which includes a vessel contacting region 138 which will contact a vessel, duct, or tissue in the event a clip is not positioned in the jaw mechanism. In FIG. 13a–13c, there is illustrated tissue stop 78 having clip stop 140 which provides a means for arresting the advancement of a clip from the clip advancing means to prevent the clip from being over-advanced to the jaw mechanism and insures the proper alignment of the clip once it is positioned in the jaws. Clip stop 140 includes a raised portion which will engage an inside surface of the clip, preferably at the bight portion, to properly align the clip within the jaws and prevent its over-advancement through the jaw mechanism. The tissue stop 78 of FIG. 13 also includes a jaw stop, which comprises a pair of raised arms 142 which engage recesses in the underside of the jaw members 75 to prevent splaying of the jaw members, as will be described below with reference to FIG. 23.

Figure 14A:
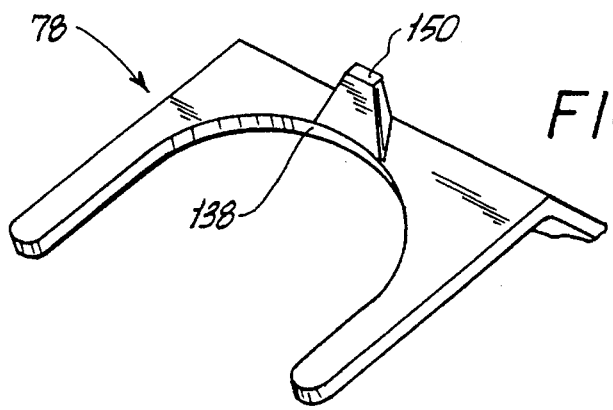
FIGS. 14a–14c illustrate another embodiment of the tissue stop of the present invention having a clip stop positioned thereon.
Figure 14B:
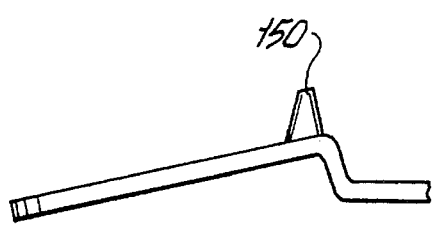
Figure 14C:
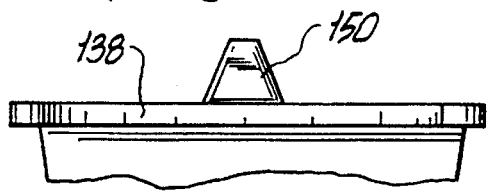

FIGS. 14a–14c disclose an alternate embodiment of the tissue stop 78 which includes an upstanding hook member 150 which comprises the clip stop for arresting the advancement of the clip into the jaw mechanism. Clip member 150 engages at least an inside surface of the clip at the bight portion to prevent over-advancement of the clip into the jaw mechanism and properly align the clip with respect to the jaw members.

Figure 15A:
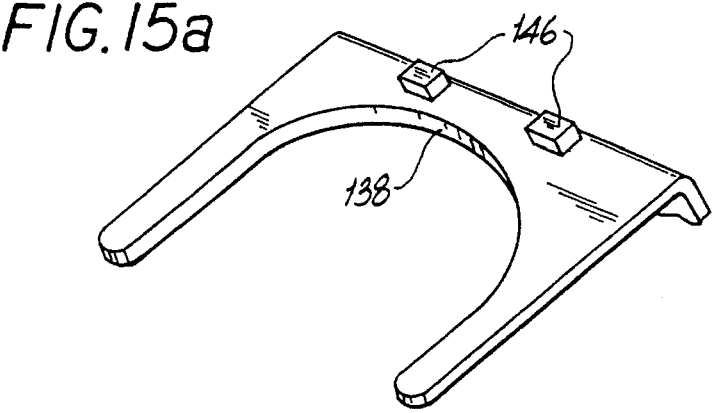
FIGS. 15a–15c illustrate another embodiment of the tissue stop of the present invention having a clip stop positioned thereon.
Figure 15B:
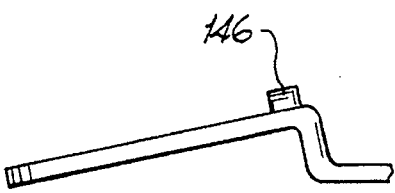
Figure 15C:
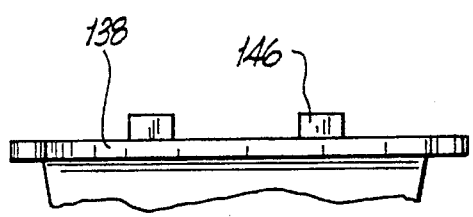

FIGS. 15a–15c illustrate a further embodiment of the clip stop assembly positioned on the tissue stop 78. In this embodiment, a pair of detents 146 are provided which engage an inside surface of the clip in the region of the bight portion to arrest its advancement into the jaw mechanism.

Figure 16A:
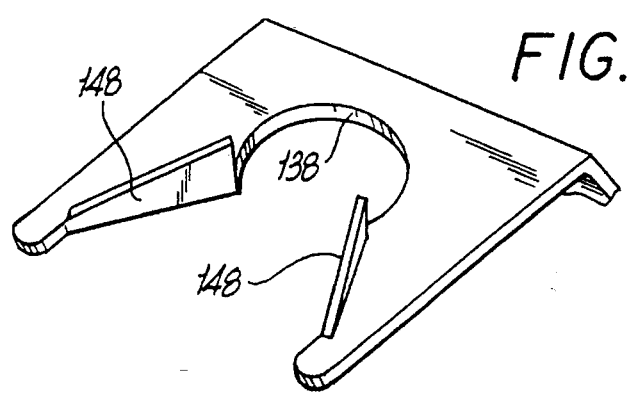
FIGS. 16a–16c illustrate a further embodiment of the tissue stop of the present invention having a clip stop positioned thereon.
Figure 16B:
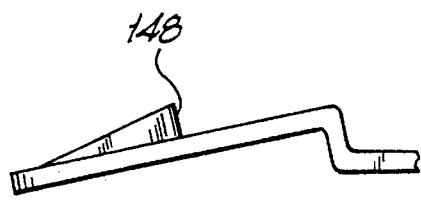
Figure 16C:
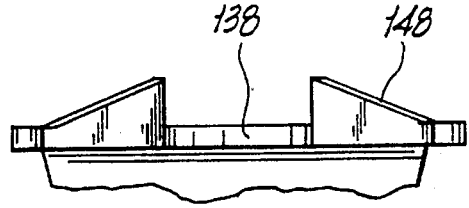
Figure 17A:
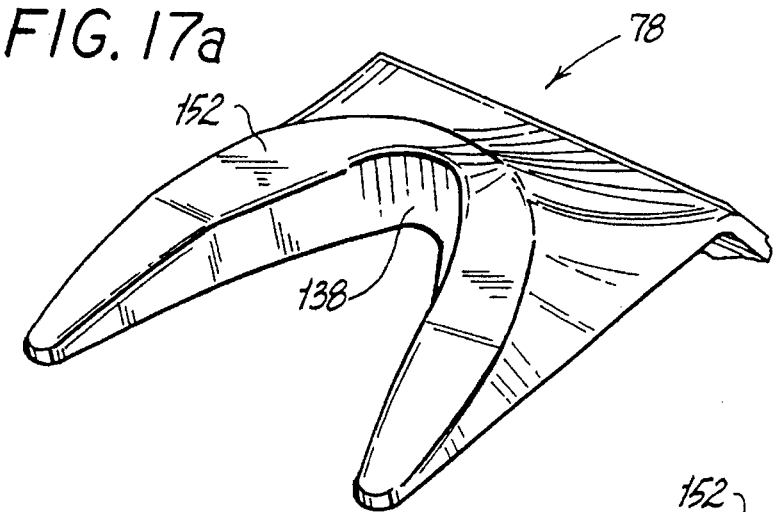
FIGS. 17a–17c illustrate a further embodiment of the tissue stop of the present invention having a clip stop positioned thereon.
Figure 17B:
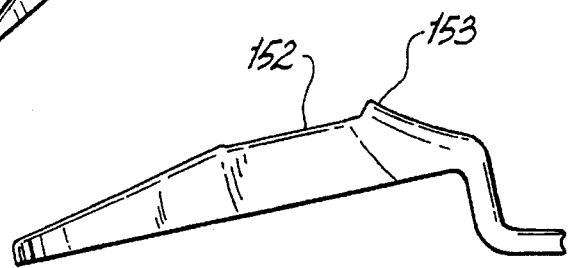
Figure 17C:
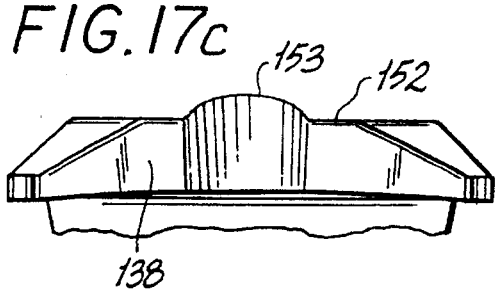

FIGS. 16a–16c show a further embodiment of the clip stop positioned on the tissue stop 78, in which a pair of upstanding walls are provided for engaging at least the inside surface of the legs of the clip as it is advanced into the jaw mechanism. A further embodiment is disclosed in FIGS. 17a–17c in which a contoured surface 152 is provided to properly align the clip in the jaw mechanism. A notch 153 is provided to engage the clip on the inside surface of the bight portion to slow the clip as it is advancing to the jaws.

Figure 18:
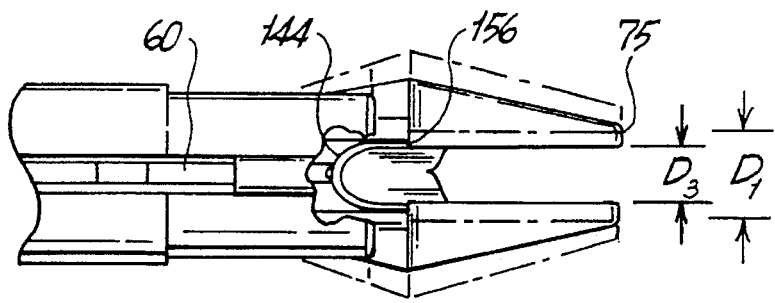
FIG. 18 illustrates the jaw mechanism of the present invention having a clip blocking member according to the present invention.

Turning now to FIG. 18, there is illustrated the clip blocking mechanism associated with the jaw members 7 5 which prevents advancement of a clip into the jaws unless the jaws are fully opened in the clip receiving position, having a gap between them at a distance $D_1$ which is indicative of the clip receiving position. As seen in FIG. 18, the jaw mechanism is shown in phantom in the fully opened, clip receiving position. A clip block member 156 is provided on each jaw member 7 5 which will engage the forward portion of the clip legs as the clip 144 is inserted into the partially closed jaws. As indicated in FIG. 18, distance $D_3$ is less than distance $D_1$ which indicates the clip receiving position.

Figure 19:
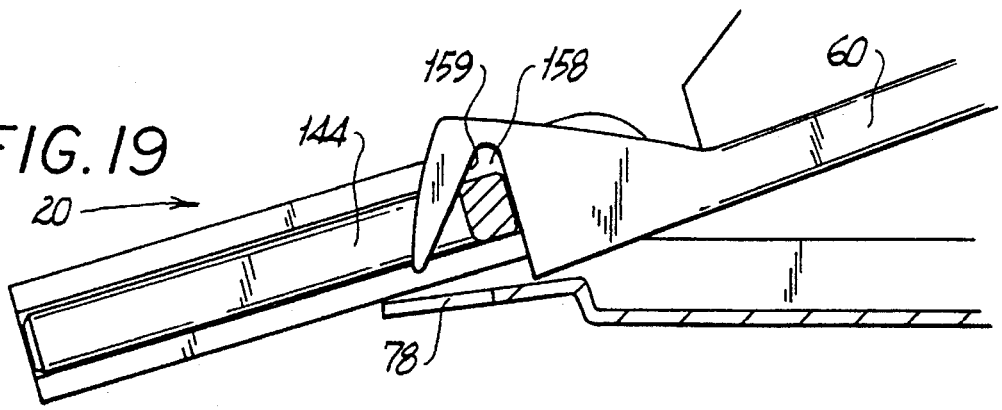
FIG. 19 illustrates a first embodiment of the pusher bar of the present invention having a clip cradling means positioned thereon.
Figure 20:
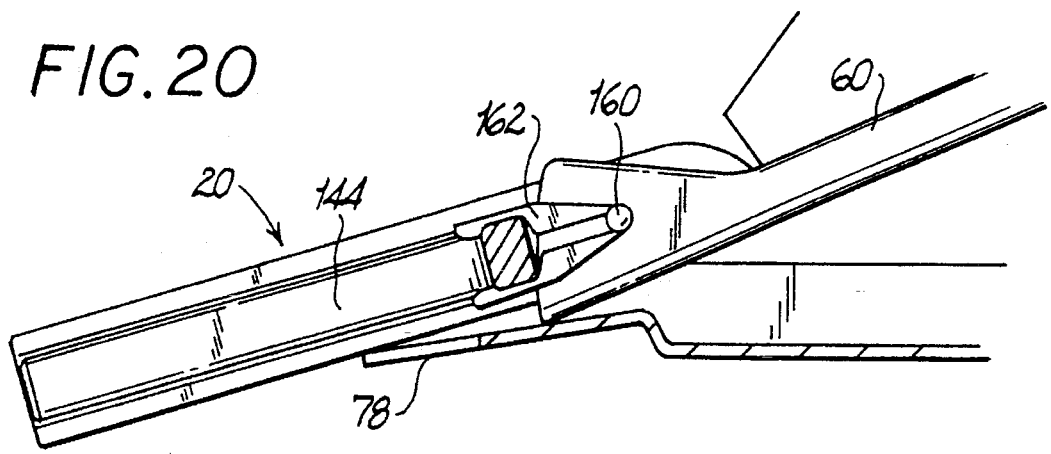
FIG. 20 illustrates the pusher bar of the present invention having an alternate embodiment of the clip cradling means.
Figure 21:
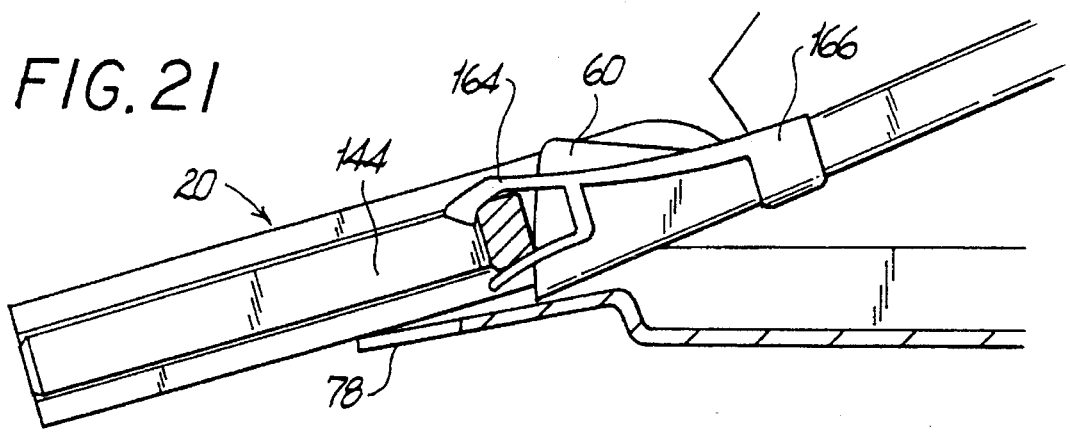
FIG. 21 illustrates a further embodiment of the pusher bar having a clip cradling means.
Figure 22:
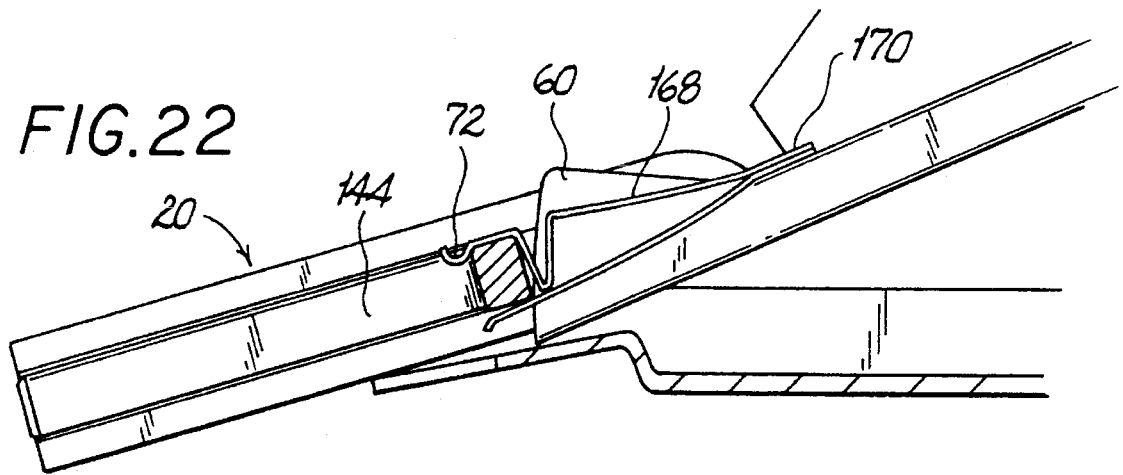
FIG. 22 illustrates the pusher bar of the present invention having a further embodiment of the clip cradling means positioned thereon.

FIG. 19 illustrates the clip engaging feature of the pusher bar 60 of the present invention. In order to prevent improper insertion of a clip into the jaw mechanism, it is desirable to provide a cradling mechanism to engage the clip and keep it in proper alignment as it is inserted into the jaws. As seen in FIG. 19, clip 144 is cradled by pusher bar 60 at the cradle notch 158 as it is inserted into jaw mechanism 20. Cradle notch 158 includes a ramped forward portion 159 which facilitates removal of the pusher bar from the jaw assembly without pulling the clip 144 out of the jaw assembly 20. An alternate embodiment of the cradling means is illustrated in FIGS. 20, 21 and 22. In FIG. 20, clip engaging fingers 162 are pivotally secured to pusher 60 at pivot pin 160. This permits some play in the clip engaging fingers 162 to insure proper alignment of the clip 144 in the jaw mechanism 20. Preferably, fingers 162 are constructed of a flexible plastic material which permits retraction of the pusher bar and fingers without dislodging the clip from the jaw mechanism. FIG. 21 illustrates a further cradling mechanism 164 which is secured to pusher bar 60 at clasp 166. It is contemplated that this embodiment can also be constructed of a flexible plastic material or a springy metal material, and may be permanently secured to pusher bar 60 or as a snap on feature when such a cradling mechanism 164 is desired. FIG. 22 shows a further embodiment of the cradling means 168, and is preferably constructed of a spring metal material which is spot welded at weld 170 and includes a flexible notch portion 172 which cradles the clip 144 but permits retraction of the pusher bar 60 without dislodging the clip 144 from the jaw mechanism 20.

Figure 23A:
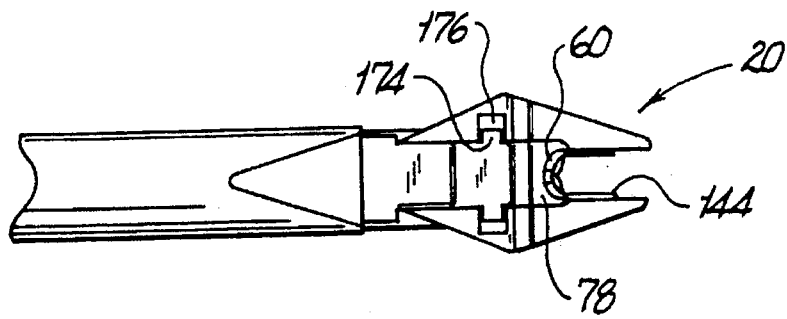
FIGS. 23a and 23b illustrate the jaw stop mechanism of the present invention.
Figure 23B:
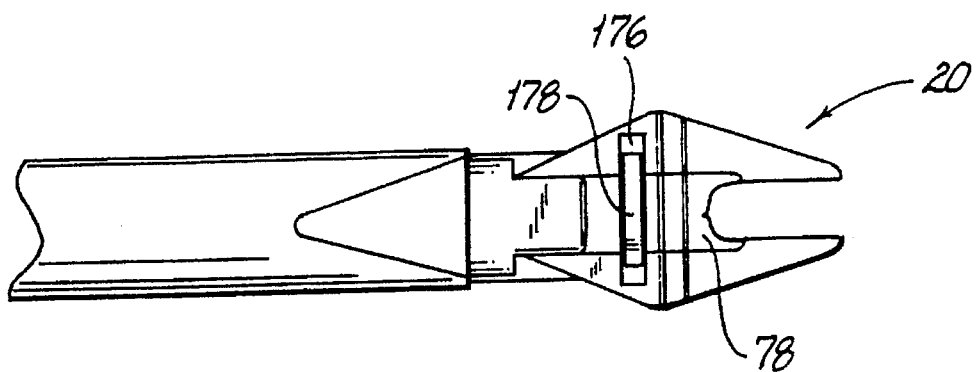

FIGS. 23a and 23b illustrate the jaw stop mechanism of the present invention. In certain surgical procedures utilizing surgical clip appliers, due to the cramped spacing inside the body during the endoscopic procedure, coupled with the sometimes distorted field of view through an endoscope or fiber optic system, application of a clip over a previously applied clip is sometimes unavoidable. When this occurs, many times the jaw mechanism may be damaged in that the individual jaw members 75 splay outwardly a distance further than the initial clip receiving distance $D_1$. When this occurs, a subsequently fed clip to the jaw mechanism may become disoriented or dislodged due to the overspacing between the jaws. In order to prevent this possibility, the instrument of the present invention provides a jaw stop mechanism which includes jaw stop bracket 174 as seen in FIG. 23a, which is part of tissue stop 78. This embodiment is similar to that shown above with respect to FIGS. 13a–13c. The bracket engages recesses 176 in the underside of the jaw members, and prevents splaying of the jaws to a distance that is greater than $D_1$. FIG. 23b illustrates a similar embodiment, in which bracket 178 is spot welded to tissue stop 78 instead of being integrally formed.

FIGS. 26 and 27 illustrate the rotation collar of the present invention. Rotation collar 22 includes the collar 22, inner sleeve 194, and outer sleeve 196. As can be seen in FIG. 27, inner sleeve 194 is positioned against body portion 18 and surrounded by outer sleeve 196, both of which are nested inside rotation collar 22. The plurality of planar surfaces which make up inner sleeve 194 cooperate with the plurality of planar surfaces 198 about the circumference of body portion 18 to provide for incremental rotation of the collar 22, and consequently the body portion 18, about a longitudinal axis of the instrument.

Collar 22 includes a plurality of indentations 192 which have a scalloped cross-section and are dimensioned and configured to accommodate the finger tip of the surgeon. The scalloped walls 193 have a sufficient height to substantially enclose the volar surface, or the finger print portion of the distal most phalange of the index finger of the surgeon. By substantially enclosing the volar surface of the finger tip of the surgeon, slippage is substantially reduced and for all practical purposes eliminated, so that single finger rotation of the body portion, and consequently the jaw mechanism is provided for the surgeon.

The surgical clip applying instrument of the present invention provides a number of novel features which enhance the performance of the instrument during laparoscopic or endoscopic surgical procedures. Each of the features of the present invention simplify the operation of the instrument and substantially eliminates inadvertent misapplication of clips during the surgical procedure. The instrument provides a visible, audible, and tactile indication of the position of the jaw members during application of a clip, particularly during application of clips during such surgical procedures as gall bladder operations.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical clips comprising:

a handle portion;

a body portion extending from said handle portion;

a jaw mechanism extending from said body portion at an end opposite said handle portion and movable between an open position for receiving a clip and a closed position for forming a clip in response to movement of said handle portion, such movement from the open to the closed position defining a closing stroke of the jaw mechanism;

a clip supply disposed within said body portion;

means for advancing a clip from said clip supply to said jaw mechanism; and means for ensuring completion of the closing stroke of said handle portion and said jaw mechanism, said means for ensuring completion of the closing stroke including means for permitting a partial opening stroke of said jaw mechanism after at least a partial closing stroke is effected to permit release of a partially formed clip from said jaw mechanism.

2. An apparatus according to claim 1, wherein said means for ensuring completion of a closing stroke includes a ratchet mechanism disposed within said handle portion, said ratchet mechanism including at least one rack member and at least one pawl member.

3. An apparatus according to claim 2, wherein said rack member has a length which corresponds to a partial closing stroke of said jaw mechanism.

4. An apparatus according to claim 1, wherein said means for ensuring a closing stroke includes a ratchet mechanism disposed within said handle portion, said ratchet mechanism including at least two rack members and at least one pawl member.

5. An apparatus according to claim 4, wherein said rack members are arranged in a series relation having a space therebetween, such that said pawl member engages and traverses a first rack member, said space, and a second rack member in sequence during the closing stroke.

6. An apparatus according to claim 5, wherein said means for permitting a partial opening stroke comprises said space between said rack members.

7. An apparatus according to claim 1, further comprising means for camming said jaw mechanism from said open position to said closed position in response to movement of said handle portion.

8. An apparatus according to claim 7, wherein said means for ensuring completion of the closing stroke includes a ratchet mechanism disposed within said handle portion, said ratchet mechanism including at least two rack members arranged in a series relation having a space therebetween and at least one pawl member, such that said pawl member engages and traverses a first rack member, said space, and a second rack member in sequence during a closing stroke of said handle portion.

9. An apparatus according to claim 8, further comprising visual indicator means associated with said camming means corresponding to said pawl member being in position at said space between said rack members, said indicator means further providing indication of a predetermined position of said jaw mechanism being between said open position and said closed position.

10. An apparatus according to claim 7, further comprising visual indicator means associated with said camming means for providing indication of a predetermined position of said jaw mechanism being between said open position and said closed position.

11. An apparatus according to claim 1, wherein said jaw mechanism comprises a pair of jaw members, said jaw members defining a gap therebetween when said jaw mechanism is in said open position.

12. An apparatus according to claim 11, further comprising means for engaging said jaw members to prevent said jaw members from being spaced apart from each other a distance which is greater than said gap defined by said jaw members in said open position.

13. An apparatus according to claim 12, wherein said engaging means comprises a bracket including a pair of tab members for engaging a portion of said jaw members to restrict splaying of said jaw members away from each other a distance greater than said gap.

14. An apparatus according to claim 12, further comprising tissue stop means disposed adjacent said jaw members for aligning said jaw members with respect to a vessel, said tissue stop means contacting said vessel only when said jaw members are devoid of a clip.

15. An apparatus according to claim 14, wherein said engaging means is integrated with said tissue stop means.

16. An apparatus according to claim 14, further comprising means disposed on said tissue stop means for arresting advancement of a clip into said jaw members, said arresting means engaging at least an inside surface of said clip during advancement to said jaw members to arrest advancement and align said clip between said jaw members.

17. An apparatus according to claim 11, further comprising means associated with said jaw members for blocking advancement of a clip into said jaw members unless said jaw members are in said open position.

18. An apparatus according to claim 11, further comprising tissue stop means disposed adjacent said jaw members for aligning said jaw members with respect to a vessel when said jaw members are devoid of a clip, said tissue stop means including clip stop means for arresting advancement of a clip into said jaw members.

19. An apparatus according to claim 18, wherein said clip stop means engages at least an inside surface of a clip to arrest advancement of said clip.

20. An apparatus according to claim 1, further comprising cradling means associated with said advancing means for engaging at least an outside surface of a clip during advancement of said clip to said jaw mechanism.

21. An apparatus according to claim 1, wherein said advancing means includes a pusher bar assembly for pushing a clip from said clip supply to said jaw mechanism.

22. An apparatus according to claim 21, further comprising means associated with said pusher bar for cradling at least an outside surface of said clip during advancement of said clip to said jaw mechanism.

23. An apparatus according to claim 22, wherein said cradling means comprises a notch in a distal end of said pusher bar, said notch being dimensioned and configured to overlay and engage at least a bight portion of said clip during advancement of said clip.

24. An apparatus according to claim 22, wherein said cradling means comprises clip engaging fingers depending from a distal end of said pusher bar, said fingers being dimensioned and configured to grasp at least a bight portion of said clip during advancement of said clip.

25. An apparatus for applying surgical clips comprising:

a handle portion;

a body portion extending from said handle portion;

a jaw mechanism extending from said body portion at an end opposite said handle portion and movable between an open position for receiving a clip and a closed position for forming a clip in response to movement of said handle portion;

a clip supply disposed within said body portion;

means for advancing a clip from said clip supply to said jaw mechanism; and a ratchet mechanism disposed within said handle portion, the ratchet mechanism retaining said jaw mechanism at incremental stages of closure over at least a partial closing stroke, said ratchet mechanism including means for permitting at least a partial opening stroke during said closing stroke to permit release of a partially formed clip from said jaw mechanism.

26. An apparatus according to claim 25, wherein said ratchet mechanism comprises a rack member and a pawl member, said pawl member being positioned on a movable handle of said handle portion, and being engageable with said rack member during said closing stroke.

27. An apparatus according to claim 26, wherein said rack member includes a plurality of teeth over a portion of a length of said rack member, a remaining portion of said length of said rack member being devoid of teeth, such that said plurality of teeth permit incremental closure and said remaining portion of said rack member permits said partial opening stroke during said closing stroke.

28. An apparatus according to claim 27, further comprising camming means responsive to movement of said handle portion for moving said jaw mechanism from said open position to said closed position, said camming means including visual indication means indicative of said pawl member being positioned on said rack at said remaining portion devoid of teeth and indicative of said camming means moving said jaw mechanism to a predetermined position between said open position and said closed position.

29. An apparatus according to claim 27, wherein said jaw mechanism is positioned at a predetermined position between said open position and said closed position when said pawl member is located at said remaining portion devoid of teeth of said rack member during said closing stroke.

30. An apparatus according to claim 26, wherein said rack member includes at least two portions each having a plurality of teeth along a length thereof, said two portions being separated by a portion of said rack member being devoid of teeth, such that said teeth permit incremental closure and said devoid portion permits said partial opening stroke during said closing stroke.

31. An apparatus according to claim 30, further comprising camming means responsive to movement of said handle portion for moving said jaw mechanism from said open position to said closed position, said camming means including visual indication means indicative of said pawl member being positioned on said rack at said portion devoid of teeth and indicative of said camming means moving said jaw mechanism to a predetermined position between said open position and said closed position.

32. An apparatus according to claim 30, wherein said jaw mechanism is positioned at a predetermined position between said open position and said closed position when said pawl member is located at said portion devoid of teeth of said rack member during said closing stroke.

33. An apparatus according to claim 26, wherein said pawl member includes means for maintaining said pawl member out of engagement with said rack member subsequent to a complete closing stroke to permit a complete opening stroke.

34. An apparatus according to claim 25, wherein said ratchet mechanism comprises a pair of rack members and a pawl member, said pawl member being positioned on a movable handle of said handle potion, and being engageable with said rack members during said closing stroke.

35. An apparatus according to claim 34, wherein said rack members include a plurality of teeth and are positioned in a series relationship with a space therebetween, such that said teeth permit incremental closure and said space permits said partial opening stroke during said closing stroke.

36. An apparatus according to claim 34, wherein said rack members include a plurality of teeth and are positioned in a parallel relationship, a first rack member having teeth over a portion of its length and a remaining portion of said length being devoid of teeth, and a second rack member having teeth over its length.

37. An apparatus according to claim 36, wherein said first rack member is engaged by said pawl member, and said second rack member is engaged by a portion of said movable handle member.

38. An apparatus for applying surgical clips comprising:

a handle portion;

a body portion extending from said handle portion;

a pair of jaw members extending from said body portion at an end opposite said handle portion and movable between an open position for receiving a clip and a closed position for forming a clip in response to movement of said handle portion, said open position defining a gap between said jaw members;

a clip supply disposed within said body portion;

means for advancing a clip from said clip supply to said jaw members;

means for camming said jaw members from said open position to said closed position;

a bracket positioned distally of said camming means to engage said jaw members to prevent said jaw members from being spaced a distance which is greater than said gap defined by said jaw members in said open position; and tissue stop means disposed adjacent said jaw members for contacting a vessel when said jaw members are devoid of a clip, said bracket being positioned on said tissue stop means.

39. An apparatus according to claim 38, further comprising means associated with said jaw members for blocking advancement of a clip into said jaw members unless said jaw members are in said open position.

40. An apparatus according to claim 39, further comprising clip stop means for arresting advancement of a clip into said jaw members, said clip stop means engaging at least an inside surface of said clip.

41. An apparatus according to claim 39, further comprising cradling means associated with said advancing means for engaging at least an outside surface of said clip during advancement of said clip to said jaw members.

42. In an apparatus for applying surgical clips, said apparatus including a handle portion, a body portion extending from said handle portion and defining a longitudinal axis, a clip supply disposed in said body portion, and means for advancing a clip from said clip supply to a jaw mechanism disposed at an end of said body portion opposite said handle portion and operable to close clips positioned therein in response to movement of said handle portion; the improvement which comprises:

the jaw mechanism including a first and second jaw member each having a clip crimping region in opposed relation and a mounting region for mounting to said body portion, said mounting region including coupling means to join said first jaw member to said second jaw member, said coupling means providing an interdigitating connection between said first and second jaw members.

43. An apparatus according to claim 42, further comprising means for blocking advancement of a clip to said jaw members when said jaw members are spaced a distance which is less than a distance defined by a gap between said jaw members when said jaw members are in said open position, said blocking means being disposed adjacent said crimping region.

44. An apparatus according to claim 42, wherein said coupling means comprises a dovetail assembly providing a plurality of cooperating sections between said jaw members.

45. An apparatus according to claim 44, wherein said dovetail assembly includes a plurality of spaces for facilitating mounting of said jaw mechanism to said body portion.

46. An apparatus according to claim 44, further comprising bracket means for preventing said jaw members from being spaced a distance which is greater than a distance defined by a gap between said jaw members when said jaw members are in said open position.

47. An apparatus for applying surgical clips comprising:

a handle portion;

a body portion extending from said handle portion;

a jaw mechanism extending from said body portion at an end opposite said handle portion and movable between an open position for receiving a clip and a closed position for forming a clip in response to movement of said handle portion;

a clip supply disposed within said body portion, each clip in said clip supply having a pair of legs depending from a bight portion extending therebetween, said bight portion having a polygonal cross-section defining a perimeter of the clip including a top portion, a bottom portion and at least one side portion;

means for advancing a clip from said clip supply to said jaw mechanism; and means associated with said advancing means for cradling said clip at said bight portion upon advancing said clip to said jaw mechanism for guiding said clip into said jaw mechanism, said cradling means engaging said side portion and at least one of said top portion and said bottom portion of said clip.

48. An apparatus according to claim 47, wherein said advancing means includes a pusher bar for advancing said clip, said pusher bar having said cradling means disposed thereon.

49. An apparatus according to claim 48, wherein said cradling means comprises a notch in a distal end of said pusher bar for overlaying at least a portion of said perimeter of said bight portion of said clip.

50. An apparatus according to claim 49, wherein said notch includes at least one ramped surface to facilitate disengagement of said pusher bar from said clip subsequent to advancement of said clip to said jaw mechanism.

51. An apparatus according to claim 48, wherein said cradling means comprises at least one clip engaging finger for overlaying at least a portion of said perimeter of said bight portion of said clip.

52. An apparatus for applying surgical clips comprising:

a handle portion;

a body portion extending from said handle portion;

a jaw mechanism extending from said body portion at an end opposite said handle portion and movable between an open position for receiving a clip and a closed position for forming a clip in response to movement of said handle portion;

a clip supply disposed within said body portion;

means for advancing a distalmost clip from said clip supply to said jaw mechanism; and means for engaging at least an inside surface of said distalmost clip subsequent to advancing said distalmost clip to a position substantially within said jaw mechanism to align said clip between jaw members of said jaw mechanism.

53. An apparatus according to claim 52, further comprising tissue stop means for contacting a vessel when said jaw mechanism is devoid of a clip, said tissue stop means having said clip engaging means disposed thereon.

54. An apparatus according to claim 53, wherein said clip engaging means comprises a raised wall surface on said tissue stop means, said wall surface engaging at least an inside surface of said clip.

55. An apparatus according to claim 53, wherein said clip engaging means comprises a tab member on said tissue stop means for engaging at least an inside surface of said clip.

56. An apparatus according to claim 53, wherein said jaw mechanism comprises a pair of jaw members, said jaw members being spaced apart in said open position and defining a clip receiving gap therebetween, said jaw members further including means for preventing splaying of said jaw members to a distance greater than said gap.

57. An apparatus according to claim 56, wherein said splaying preventing means comprises a bracket disposed on said tissue stop means, said bracket comprising a pair of tab members which engage recess in said jaw members.

58. An apparatus according to claim 52, wherein said clip engaging means comprises a tab member disposed on a distal end of said body portion for engaging at least an inside surface of said clip.

59. An apparatus according to claim 52, further comprising clip stop means disposed on said jaw mechanism for preventing advancement of a clip to said jaw mechanism when said jaw mechanism is not in said open position.

60. An apparatus for applying surgical clips comprising:

a handle portion including at least one handle member movable with respect to another handle member;

a body portion extending from said handle portion;

a pair of jaw members extending from said body portion at an end opposite said handle portion and movable between an open position for receiving a clip and a closed position for forming a clip in response to movement of at least one movable handle, said open position defining a gap between said jaw members;

a clip supply disposed within said body portion;

means for advancing a clip from said clip supply to said jaw members;

means for camming said jaw members from said open position to said closed position in response to movement of at least one movable handle; and an indicator member operably associated with said camming means, said indicator member indicating at least one distance between said jaw members which is greater than a distance defined by said closed position and less than said gap of said open position;

wherein said camming means comprises a slidable channel disposed in said body portion and an advancement tube disposed in said handle portion for sliding said channel to cam said jaw members from said open position to said closed position in response to movement of at least said ode movable handle; and wherein said indicator member comprises a flag disposed on said advancement tube, and an aperture in said handle portion for displaying said flag when said jaw members are spaced said predetermined distance.

61. An apparatus according to claim 60, further comprising a rack and pawl mechanism disposed in said handle portion, said pawl being engaged with said rack during at least a partial closing stroke of at least said one movable handle, said pawl being disengaged when said flag is positioned in said aperture to permit at least a partial opening stroke of at least said one movable handle.

62. An apparatus for applying surgical clips comprising:

a handle portion including a housing and at least one pivoting handle;

a body portion extending from said handle portion a pair of jaw members extending from said body portion at an end opposite said handle portion and movable between an open position for receiving a clip and a closed position for forming a clip in response to movement of said pivoting handle, said open position defining a gap between said jaw members;

a clip supply disposed within said body portion;

means for advancing a clip from said clip supply to said jaw members;

means for camming said jaw members in response to movement of said pivoting handle from said open position to said closed position; and an indicator operably associated with said housing of said handle portion, said indicator indicating at least one distance between said jaw members which is greater than a distance defined by said closed position and less than said gap of said open position;

wherein said indicator comprises an aperture on said handle portion for displaying a flag disposed on said camming means, said flag being disposed in said aperture when said jaw members are spaced said predetermined distance.

63. An apparatus for applying surgical clips comprising:

a handle portion including a housing and at least one pivoting handle;

a body portion extending from said handle portion;

a pair of jaw members extending from said body portion at an end opposite said handle portion and movable between an open position for receiving a clip and a closed position for forming a clip in response to movement of said pivoting handle, said open position defining a gap between said jaw members;

a clip supply disposed within said body portion;

means for advancing a clip from said clip supply to said jaw members;

means for camming said jaw members in response to movement of said pivoting handle from said open position to said closed position;

an indicator operably associated with said housing of said handle portion, said indicator indicating at least one distance between said jaw members which is greater than a distance defined by said closed position and less than said gap of said open position;

wherein said indicator comprises a clutch mechanism disposed on said pivoting handle for engaging said housing during a portion of pivoting movement, said clutch mechanism providing tactile indication of said jaw members being spaced said predetermined distance.

64. An apparatus according to claim 63, wherein said clutch mechanism includes a block member extending from said pivoting handle towards said housing, said block member contacting said housing when said jaw members are spaced said predetermined distance.

65. An apparatus according to claim 64, wherein said block member is movable between an armed position and a disarmed position, said block member including means for automatically moving said block member from said armed position to said disarmed position.

66. An apparatus according to claim 65, wherein said automatic means disarms said block member upon release of a force on said block member corresponding to said block member contacting said housing.

67. An apparatus for applying surgical clips comprising:

a handle portion including a housing and at least one pivoting handle;

a body notion extending from said handle portion;

a jaw mechanism extending from said body portion at an end opposite said handle portion and movable between an open position for receiving a clip and a closed position for forming a clip in response to movement of said pivoting handle;

a clip surgically disposed within said body portion;

means for advancing a clip from said clip supply to said jaw mechanism;

means for camming said jaw mechanism from said open position to said closed position response to movement of said pivoting handle;

a visual indicator on said housing, the visual indicator providing visual indication of a predetermined position of said jaw mechanism between said open position and said closed position; and audible indication means associated with said handle portion for providing audio indication of said predetermined position of said jaw mechanism between said open position and said closed position.

68. An apparatus according to claim 67, wherein said audible indication means comprises a rack and pawl mechanism disposed within said handle portion, said pawl being engaged with said rack when said jaw mechanism is out of said predetermined position, and said pawl being disengaged from said rack when said jaw mechanism is in said predetermined position.

69. An apparatus according to claim 68, wherein said rack includes a plurality of teeth, at least a portion of said rack being devoid of teeth, such that when said pawl is in a position on said rack corresponding to said portion devoid of teeth, said jaw mechanism is in said predetermined position.

70. An apparatus according to claim 67, wherein said audible indication means comprises a sound generator positioned in said handle portion and including a power source, said sound generator being actuated by switch means engaged by movement of said pivoting handle when said jaw mechanism is in said predetermined position.

71. An apparatus for applying surgical clips comprising:

a handle portion including a housing and at least one pivoting handle;

a body portion extending from said handle portion;

a jaw mechanism extending from said body portion at an end opposite said handle portion and movable between an open position for receiving a clip and a closed position for forming a clip in response to movement of said pivoting handle;

a clip supply disposed within said body portion;

means for advancing a clip from said clip supply to said jaw mechanism;

means for camming said jaw mechanism from said open position to said closed position in response to movement of said pivoting handle; and a visual indicator on said housing, the visual indicator providing visual indication of a predetermined position of said jaw mechanism between said open position and said closed position;

wherein said visual indicator comprises an aperture on said handle portion for displaying a flag disposed on said camming means, said flag being disposed in said aperture when said jaw mechanism is in said predetermined position.

72. An apparatus for applying surgical clips comprising:

a handle portion including a housing and at least one pivoting handle;

a body portion extending from said handle portion;

a jaw mechanism extending from said body portion at an end opposite said handle portion and movable between an open position for receiving a clip and a closed position for forming a clip in response to movement of said pivoting handle;

a clip supply disposed within said body portion;

means for advancing a clip from said clip supply to said jaw mechanism;

means for camming said jaw mechanism from said open position to said closed position in response to movement of said pivoting handle; and a visual indicator on said housing, the visual indicator providing visual indication of a predetermined position of said jaw mechanism between said open position and said closed position;

wherein said visual indicator comprises a light indicator positioned on said handle potion and including a power source, said light indicator being actuated by switch means engaged by movement of said handle portion when said jaw mechanism is in said predetermined position.

73. An apparatus for applying surgical clips comprising:

a handle portion;

a body portion extending from said handle portion;

a jaw mechanism extending from said body portion at an end opposite said handle portion and movable between an open position for receiving a clip and a closed position for forming a clip in response to movement of said handle portion;

a clip supply disposed within said body portion;

means for advancing a clip from said clip supply to said jaw mechanism;

means for camming said jaw mechanism from said open position to said closed position in response to movement of said handle portion; and audible indication means associated with said handle portion for providing audio indication of a predetermined position of said jaw mechanism between said open position and said closed position.

74. An apparatus according to claim 73, wherein said audible indication means comprises a sound generator positioned in said handle portion and including a power source, said sound generator being actuated by switch means engaged by movement of said handle portion when said jaw mechanism is in said predetermined position.

* * * * *